(12) United States Patent
Pyon et al.

(10) Patent No.: US 10,177,160 B2
(45) Date of Patent: Jan. 8, 2019

(54) SEMICONDUCTOR DEVICE AND METHOD OF FABRICATING THE SAME

(71) Applicant: SAMSUNG ELECTRONICS CO., LTD., Suwon-si, Gyeonggi-do (KR)

(72) Inventors: Youngbeom Pyon, Suwon-si (KR); Kichul Park, Changwon-si (KR); Inkwon Kim, Hwaseong-si (KR); Ki Hoon Jang, Hwaseong-si (KR); Byoungho Kwon, Hwaseong-si (KR); Sangkyun Kim, Hwasoeng-si (KR); Boun Yoon, Seoul (KR)

(73) Assignee: SAMSUNG ELECTRONICS CO., LTD., Suwon-si, Gyeonggi-do (KR)

( * ) Notice: Subject to any disclaimer, the term of this patent is extended or adjusted under 35 U.S.C. 154(b) by 0 days.

(21) Appl. No.: 15/661,280

(22) Filed: Jul. 27, 2017

(65) Prior Publication Data
US 2018/0166454 A1 Jun. 14, 2018

(30) Foreign Application Priority Data
Dec. 8, 2016 (KR) ........................ 10-2016-0166910

(51) Int. Cl.
| | |
|---|---|
| *H01L 21/00* | (2006.01) |
| *H01L 23/528* | (2006.01) |
| *H01L 27/112* | (2006.01) |
| *H01L 23/535* | (2006.01) |
| *H01L 27/11551* | (2017.01) |
| *H01L 27/11578* | (2017.01) |
| *H01L 21/768* | (2006.01) |
| *H01L 21/02* | (2006.01) |
| *H01L 23/538* | (2006.01) |

(52) U.S. Cl.
CPC ...... *H01L 27/11286* (2013.01); *H01L 23/528* (2013.01); *H01L 23/535* (2013.01); *H01L 27/112* (2013.01); *H01L 27/11551* (2013.01); *H01L 27/11578* (2013.01); *H01L 21/02107* (2013.01); *H01L 21/76801* (2013.01); *H01L 23/538* (2013.01)

(58) Field of Classification Search
CPC ......... H01L 21/02107; H01L 21/76801; H01L 23/528
See application file for complete search history.

(56) References Cited

U.S. PATENT DOCUMENTS

| | | | | |
|---|---|---|---|---|
| 6,291,367 | B1 * | 9/2001 | Kelkar | H01L 21/02107 257/E21.243 |
| 7,179,735 | B2 * | 2/2007 | Kim | H01L 21/02107 257/E21.243 |
| 8,394,716 | B2 * | 3/2013 | Hwang | H01L 27/11551 257/315 |

(Continued)

*Primary Examiner* — David Zarneke
(74) *Attorney, Agent, or Firm* — Lee & Morse P.C.

(57) ABSTRACT

A semiconductor device includes a substrate, a peripheral structure, a lower insulating layer, and a stack. The substrate includes a peripheral circuit region and a cell array region. The peripheral structure is on the peripheral circuit region. The lower insulating layer covers the peripheral circuit region and the cell array region and has a protruding portion protruding from a flat portion. The stack is on the lower insulating layer and the cell array region, and includes upper conductive patterns and insulating patterns which are alternately and repeatedly stacked.

20 Claims, 40 Drawing Sheets

(56) References Cited

U.S. PATENT DOCUMENTS

| | | | |
|---|---|---|---|
| 8,497,537 B2* | 7/2013 | Wang | H01L 27/11507 |
| | | | 257/295 |
| 8,664,101 B2 | 3/2014 | Kim et al. | |
| 8,822,287 B2 | 9/2014 | Kim et al. | |
| 8,927,359 B2* | 1/2015 | Liu | H01L 21/02107 |
| | | | 438/199 |
| 9,087,861 B2 | 7/2015 | Hwang et al. | |
| 9,224,747 B2 | 12/2015 | Mizutani et al. | |
| 9,425,208 B2 | 8/2016 | Kim et al. | |
| 9,431,418 B2* | 8/2016 | Jung | H01L 27/11582 |
| 9,478,561 B2* | 10/2016 | Kim | H01L 27/11575 |
| 9,953,999 B2* | 4/2018 | Nam | H01L 27/11519 |
| 2001/0001191 A1* | 5/2001 | Liu | C23C 16/50 |
| | | | 204/192.22 |
| 2004/0266221 A1* | 12/2004 | Kim | H01L 21/02107 |
| | | | 438/788 |
| 2011/0115000 A1* | 5/2011 | Yang | H01L 21/823807 |
| | | | 257/288 |
| 2015/0340374 A1 | 11/2015 | Jung et al. | |
| 2015/0348987 A1 | 12/2015 | Lee et al. | |
| 2016/0027795 A1 | 1/2016 | Jung et al. | |
| 2016/0049423 A1 | 2/2016 | Yoo et al. | |

* cited by examiner

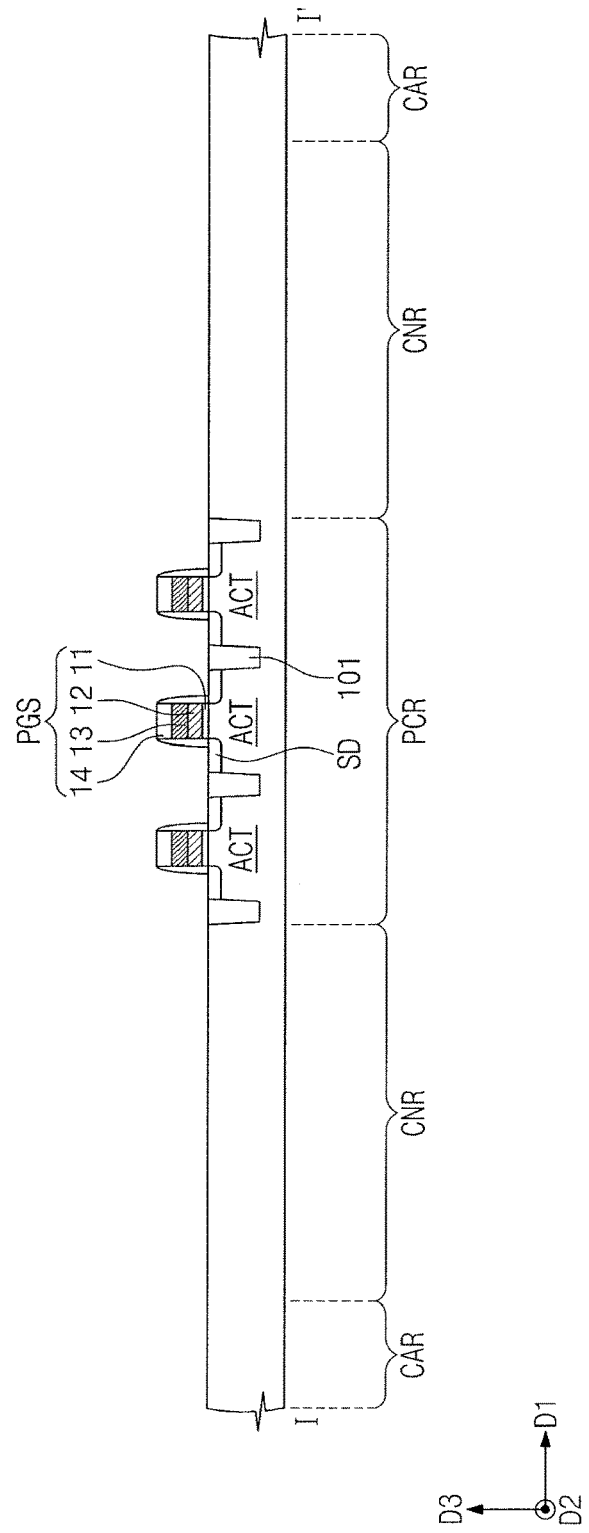

SEMICONDUCTOR DEVICE AND METHOD OF FABRICATING THE SAME

CROSS-REFERENCE TO RELATED APPLICATIONS

Korean Patent Application No. 10-2016-0166910, filed on Dec. 8, 2016, and entitled, "Semiconductor Device and Method of Fabricating the Same," is incorporated by reference herein in its entirety.

BACKGROUND

1. Field

One or more embodiments described herein relate to a semiconductor device and method for fabricating a semiconductor device.

2. Description of the Related Art

Efforts are being made to increase the integration of semiconductor devices. The integration of a two-dimensional (or planar) semiconductor device is mainly determined by the area of its unit memory cells and the sizes of fine patterns within those cells. Extremely expensive process equipment must be used to form these fine patterns.

SUMMARY

In accordance with one or more embodiments, a semiconductor device includes a substrate including a peripheral circuit region and a cell array region; a peripheral structure on the peripheral circuit region; a lower insulating layer covering the peripheral circuit region and the cell array region, the lower insulating layer on the peripheral circuit region having a flat portion and a protruding portion protruding from the flat portion; and a stack on the lower insulating layer and on the cell array region, wherein the stack includes upper conductive patterns and insulating patterns which are alternately and repeatedly stacked.

In accordance with one or more other embodiments, a semiconductor device includes a substrate including a peripheral circuit region and a cell array region; a peripheral structure on the peripheral circuit region; a lower insulating layer covering the peripheral circuit region and the cell array region and having a protruding portion on the peripheral structure; and a stack on the lower insulating layer and on the cell array region, wherein the stack includes upper conductive patterns and insulating patterns that are alternately and repeatedly stacked and wherein a level of a top surface of the protruding portion is higher than a level of a top surface of a lowermost one of the insulating patterns of the stack.

In accordance with one or more other embodiments, a method of fabricating a semiconductor device including providing a substrate including a peripheral circuit region and a cell array region; forming a peripheral structure on the peripheral circuit region; forming a lower insulating layer to cover the peripheral structure and the cell array region, the lower insulating layer having a lower protruding portion on the peripheral structure; forming a mold structure on the cell array region, the mold structure including upper sacrificial patterns and insulating patterns that are alternately and repeatedly stacked on the lower insulating layer; forming an etch stop pattern on the mold structure; forming an upper insulating layer to cover the lower protruding portion, the mold structure, and the etch stop pattern; and partially removing the upper insulating layer to expose the etch stop pattern.

In accordance with one or more other embodiments, a method for fabricating a semiconductor device includes forming a first insulation layer on a substrate; forming a stack on the first insulation layer, the stack including alternating conductive patterns and insulating patterns which are adjacent to a protruding gate structure on the substrate; forming a second insulation layer on the stack and the protruding gate structure, an upper surface of the second insulation layer including a protrusion corresponding to the protruding gate structure; and removing a portion of the second insulation layer including the protrusion.

BRIEF DESCRIPTION OF THE DRAWINGS

Features will become apparent to those of skill in the art by describing in detail exemplary embodiments with reference to the attached drawings in which.

DETAILED DESCRIPTION

Figure 1:
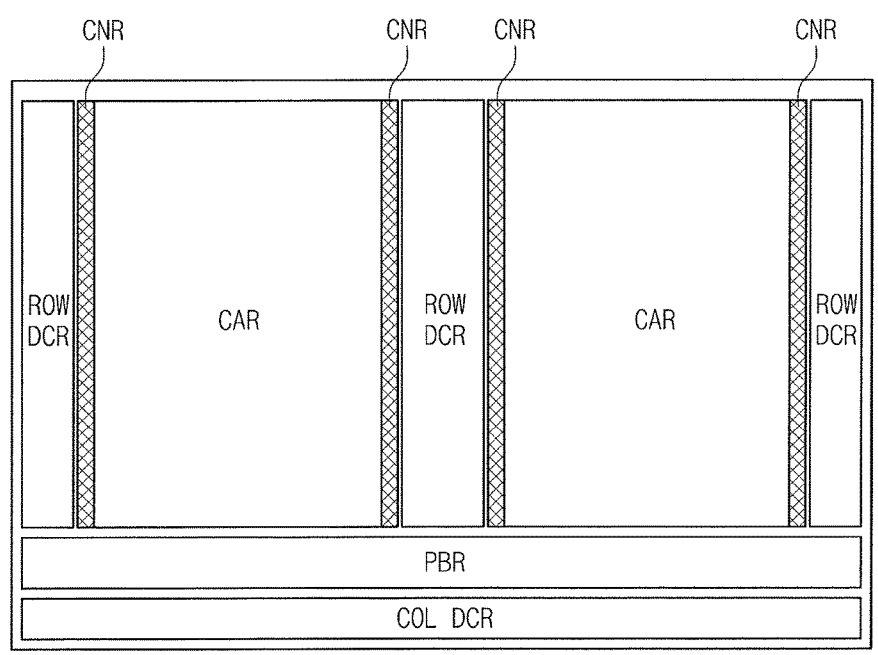
FIG. 1 illustrates an embodiment of a three-dimensional semiconductor device.

FIG. 1 illustrates an embodiment of a three-dimensional semiconductor device, which, for example, may include three-dimensionally arranged memory cells. Referring to FIG. 1, a three-dimensional semiconductor device may include cell array regions CAR and a peripheral circuit region. The peripheral circuit region may include row decoder regions ROW DCR, a page buffer region PBR, a column decoder region COL DCR, and a control circuit region. In some embodiments, connection regions CNR may be respectively provided between the cell array regions CAR and the row decoder regions ROW DCR.

A memory cell array with a plurality of memory cells may be on the cell array region CAR. The memory cell array may include memory cells and a plurality of word and bit lines electrically connected to the memory cells. The memory cells may be arranged in a three-dimensional pattern in the semiconductor device.

In each of the row decoder regions ROW DCR, a row decoder may select at least one of the word lines in the memory cell array. An interconnection structure in the connection region CNR may electrically connect the memory cell array to the row decoder. The row decoder may select one of the word lines based on address information and may apply different word line voltages to selected and unselected ones of the word lines, based on control signals from a control circuit.

In the page buffer region PBR, a page buffer may be provided to read out data stored in the memory cells. Depending on an operation mode, the page buffer may be configured to temporarily store data in the memory cells or to sense data stored in the memory cells. For example, the page buffer may serve as a write driver in a program operation mode or as a sense amplifier in a read operation mode.

A column decoder may be in the column decoder region COL DCR and connected to the bit lines of the memory cell array. The column decoder may also be used as a data transmission path between the page buffer and an external device, e.g., a memory controller.

Figure 2:
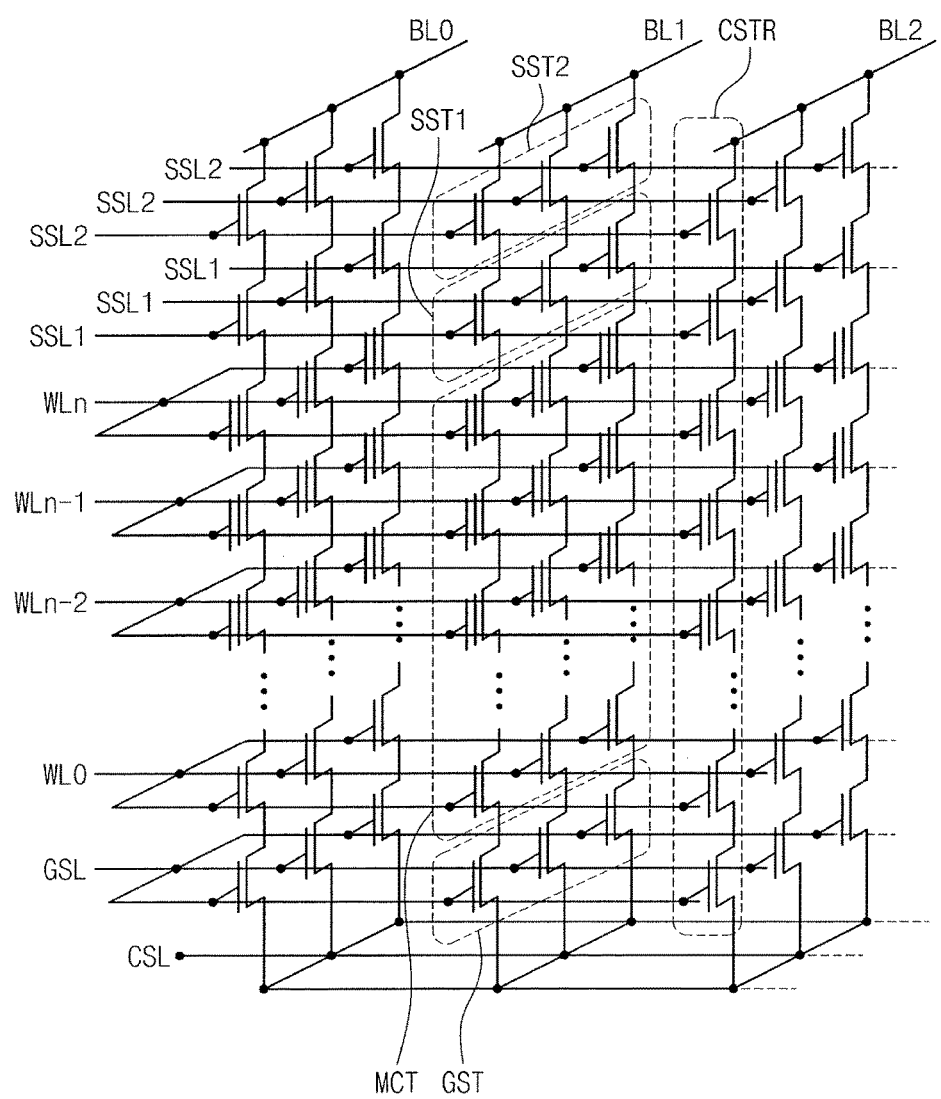
FIG. 2 illustrates an embodiment of a memory cell array.

FIG. 2 illustrates an embodiment of a memory cell array, which, for example, may be included in the three-dimensional semiconductor device of FIG. 1. Referring to FIG. 2, the memory cell array may include a common source line CSL, a plurality of bit lines BL0-BL2, and a plurality of cell strings CSTR between the common source line CSL and the bit lines BL0-BL2.

The bit lines BL0-BL2 may be arranged in a two-dimensional pattern. A plurality of the cell strings CSTR may be connected in parallel to each of the bit lines BL0-BL2. The cell strings CSTR may be connected in common to the common source line CSL. In other words, a plurality of the cell strings CSTR may be between the bit lines BL0-BL2 and the common source line CSL.

In certain embodiments, a plurality of the common source lines CSL may be arranged in a two-dimensional pattern. Thus, it may be possible to apply the same source voltage to the common source lines CSL or to apply at least two different source voltages to each of the common source lines CSL.

Each of the cell strings CSTR may include string selection transistors SST1 and SST2, memory cells MCT, and at least one ground selection transistor GST connected in series to each other. Each memory cell MCT may include a data storage element.

As an example, each cell string CSTR may include first and second string selection transistors SST1 and SST2, which are connected in series to each other. Each second string selection transistor SST2 may be coupled to a corresponding one of the bit lines BL0-BL2. The ground selection transistor GST may be coupled to the common source line CSL. The memory cells MCT may be between the first string selection transistor SST1 and the ground selection transistor GST and may be connected in series to each other.

As another example, in each cell string CSTR, the ground selection transistor GST may include a plurality of transistors connected in series to each other, similar to the string selection transistors SST1 and SST2. In one embodiment, only one string selection transistor may be in each of the cell strings CSTR.

The first string selection transistor SST1 may be controlled by a first string selection line SSL1. The second string selection transistor SST2 may be controlled by a second string selection line SSL2. The memory cells MCT may be controlled by a plurality of word lines WL0-WLn. The ground selection transistor GST may be controlled by a ground selection line GSL. The common source line CSL may be connected in common to source electrodes of the ground selection transistors GST.

Since each cell string CSTR may have a multi-layered structure which includes a plurality of memory cells MCT at different heights from the common source lines CSL and the word lines WL0-WLn provided between the common source lines CSL and the bit lines BL0-BL2.

In some embodiments, as illustrated in FIG. 2, gate electrodes of the memory cells MCT may be at substantially the same height from the common source lines CSL and may be connected in common to one of the word lines WL0-WLn, and thus may be in an equipotential state. In certain embodiments, unlike that shown in FIG. 2, the gate electrodes of the memory cells MCT may be at substantially the same height from the common source lines CSL, but some (e.g., in different rows or columns) of them may be independently controlled.

Figure 3:
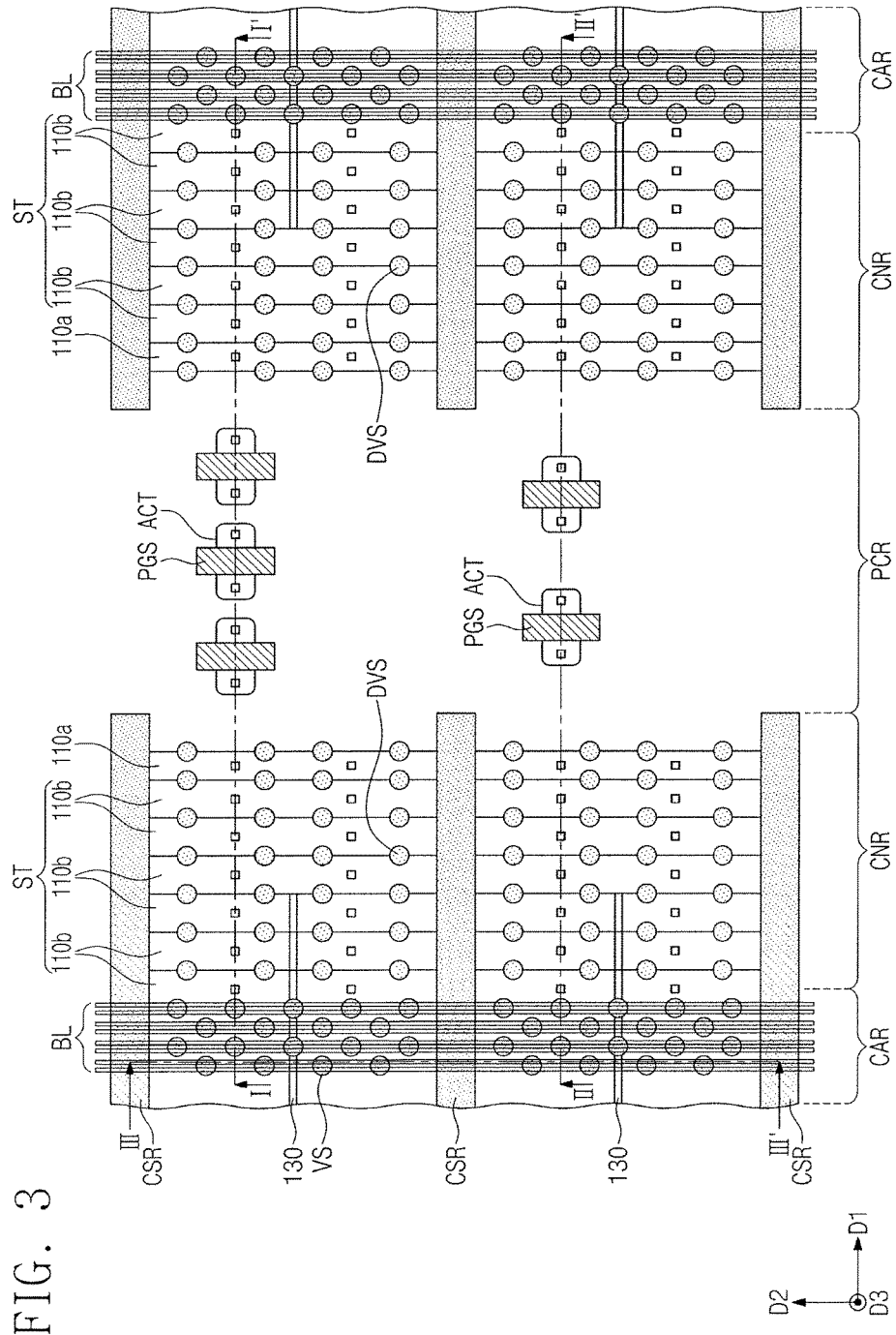
FIG. 3 illustrates another view of the three-dimensional semiconductor device.
Figure 4A:
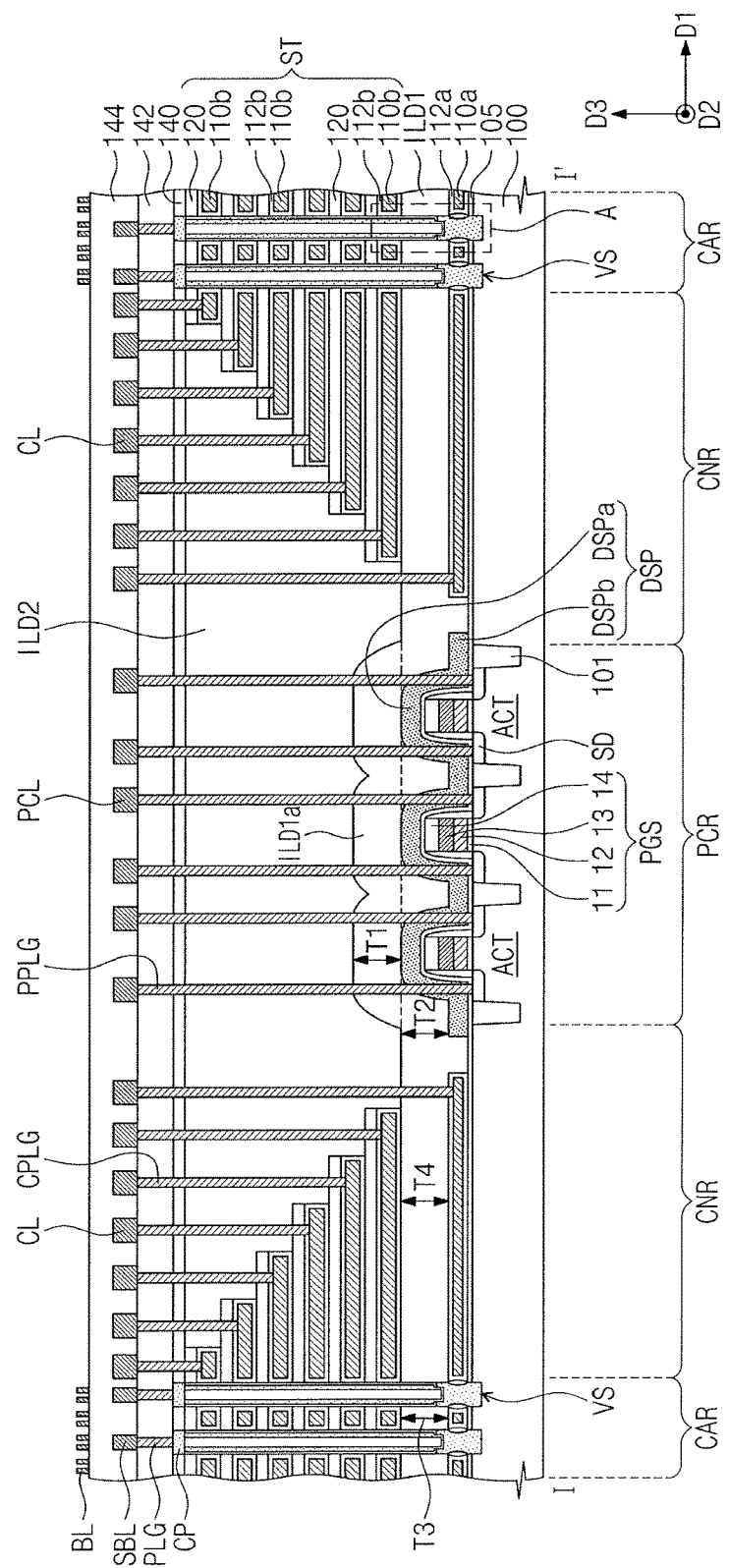
FIGS. 4A-4C illustrate sectional view embodiments of the three-dimensional semiconductor device.
Figure 4B:
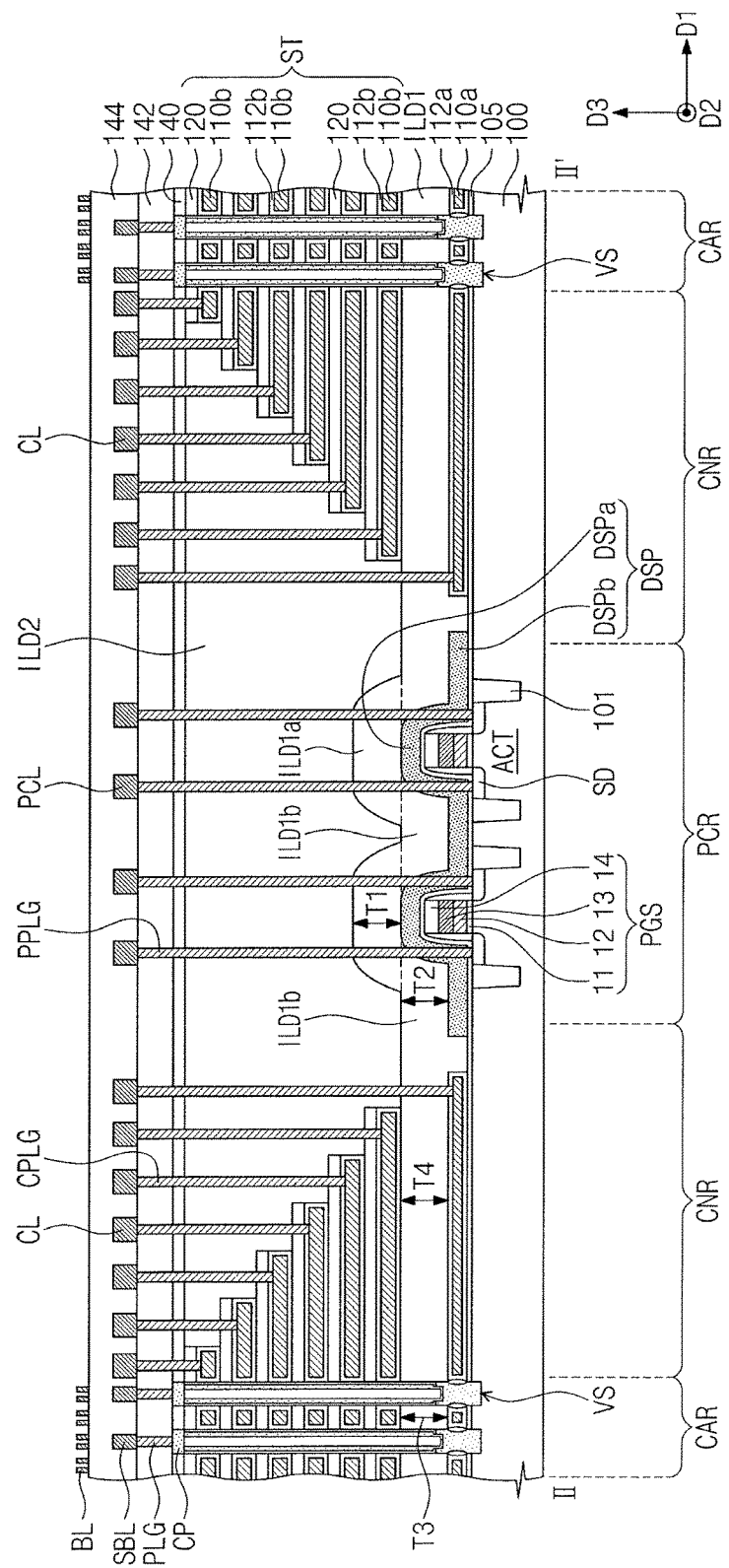
Figure 4C:
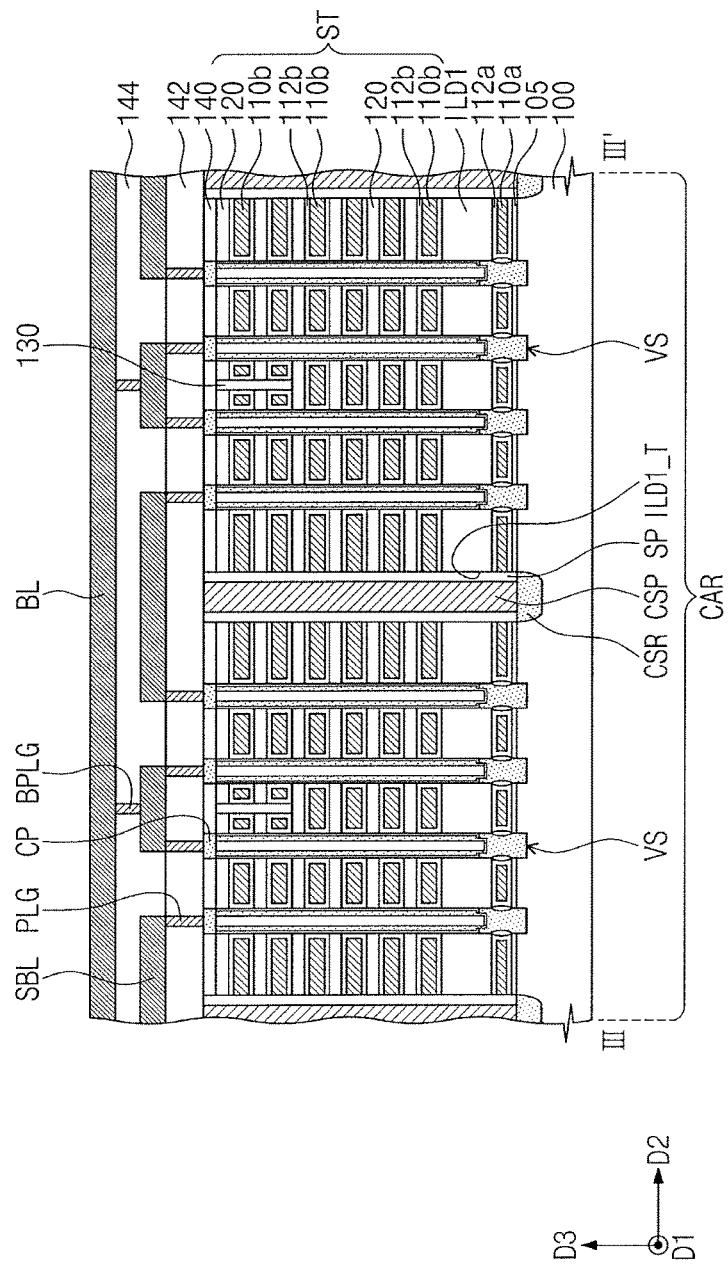
Figure 5:
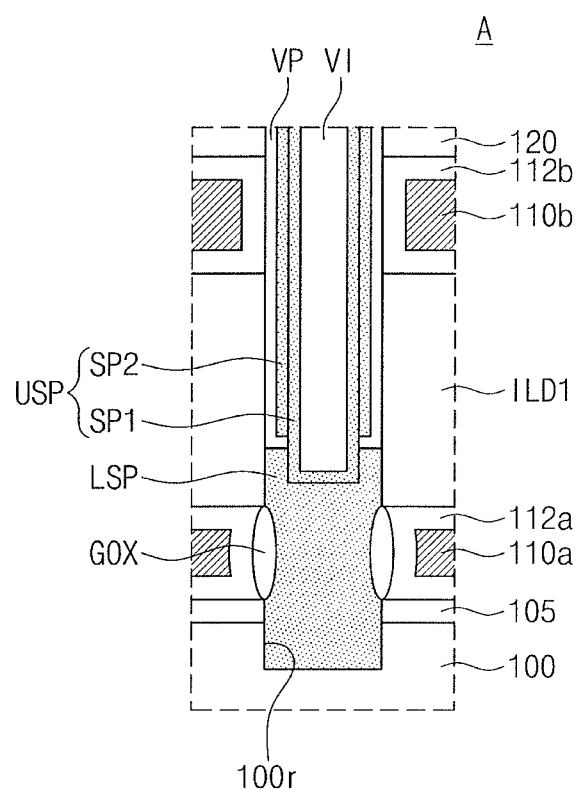
FIG. 5 illustrates an enlarged view of portion A in FIG. 4A.

FIG. 3 illustrates a plan view of a three-dimensional semiconductor device, which, for example, may be the semiconductor device in FIGS. 1 and/or 2. FIGS. 4A to 4C are sectional views illustrating a three-dimensional semiconductor device. For example, FIG. 4A illustrates a sectional view taken along line I-I' of FIG. 3. FIG. 4B illustrates a sectional view taken along line II-II' of FIG. 3. FIG. 4C illustrates a sectional view taken along line III-III' of FIG. 3. FIG. 5 illustrates an enlarged view of a portion 'A' of FIG. 4A.

Referring to FIGS. 3, 4A to 4C, and 5, a substrate 100 may include cell array regions CAR, a peripheral circuit region PCR, and connection regions CNR. The cell array regions CAR may be spaced apart from each other in a first direction D1. The peripheral circuit region PCR may be between adjacent ones of the cell array regions CAR. Each connection region CNR may be between a corresponding one of the cell array regions CAR and the peripheral circuit region PCR.

The substrate 100 may be one of a single crystalline silicon layer, a single crystalline germanium layer, a silicon layer on a germanium layer, a silicon layer on an insulation layer, or a polycrystalline semiconductor layer on an insulation layer. The substrate 100 may be, for example, a silicon wafer of a first conductivity type (e.g., p-type).

A peripheral structure may be on the peripheral circuit region PCR. As described with reference to FIG. 1, the peripheral structure may include row and column decoders, a page buffer, and/or control circuits that write or read data in or from the memory cells.

The peripheral structure may include peripheral gate stacks PGS on the peripheral circuit region PCR. The peripheral gate stacks PGS may be spaced apart from each other. Each peripheral gate stack PGS may cross an active region ACT which is in the peripheral circuit region PCR and which is defined by a device isolation layer 101.

In one embodiment, each peripheral gate stack PGS may include a gate insulating pattern 11, a poly silicon pattern 12, a metal pattern 13, and a hard mask pattern 14 sequentially stacked on the substrate 100. Spacers 15 may cover side surfaces of each of the peripheral gate stacks PGS. Source/drain regions SD may be in portions of the active region ACT located at different sides of each of the peripheral gate stacks PGS.

A buffer insulating layer 105 may cover the substrate 100 provided with the peripheral structure. The buffer insulating layer 105 may conformally cover the peripheral gate stacks PGS on the peripheral circuit region PCR and may extend to cover the connection regions CNR and cell array regions CAR. The buffer insulating layer 105 may formed of or include, for example, silicon oxide.

A dummy sacrificial pattern DSP may be on the peripheral circuit region PCR to cover the peripheral structure. The dummy sacrificial pattern DSP may be on the buffer insulating layer 105, may conformally cover the peripheral gate stacks PGS, and may not extend to the cell array regions CAR. The dummy sacrificial pattern DSP may include protruding portions DSPa on the peripheral gate stacks PGS and extended portion DSPb overlapping the peripheral circuit region PCR but not the peripheral gate stacks PGS. Top surfaces of the protruding portions DSPa of the dummy sacrificial pattern DSP may be at a level higher than that of the extended portion DSPb. The dummy sacrificial pattern DSP may include a material having an etch selectivity with respect to the buffer insulating layer 105. For example, the dummy sacrificial pattern DSP may be formed of or include silicon nitride or silicon oxynitride.

Lower conductive patterns 110*a* may be provided on the buffer insulating layer 105 and on the cell array regions CAR. Each of the lower conductive patterns 110*a* may be located at substantially the same level as the extended portion DSPb of the dummy sacrificial pattern DSP. The lower conductive patterns 110*a* may be spaced apart from each other, in a second direction D2 crossing the first direction D1, on each cell array region CAR. Each lower conductive pattern 110*a* on the cell array region CAR may cover the connection region CNR, but may not cover the peripheral circuit region PCR. Each lower conductive pattern 110*a* may be used as the ground selection line GSL, for example, as described with reference to FIG. 2. The lower conductive patterns 110*a* may be formed of or include at least one of metals (e.g., W, Al, Ti, Ta, Co, and Cu) or metal nitrides (e.g., TiN, TaN, and WN).

A lower insulating layer ILD1 may cover the substrate 100 provided with the dummy sacrificial pattern DSP and the lower conductive patterns 110*a*. The lower insulating layer ILD1 may conformally cover the dummy sacrificial pattern DSP and the lower conductive patterns 110*a*. The lower insulating layer ILD1 may have trenches ILD1_T on the cell array regions CAR. As shown in FIG. 4C, side surfaces of the trenches ILD1_T of the lower insulating layer ILD1 may be aligned to side surfaces of the lower conductive patterns 110*a*, which are provided to face each other in the second direction D2. When viewed in a plan view, each trench ILD1_T may extend from the cell array region CAR to the connection region CNR, but not to the peripheral circuit region PCR.

The lower insulating layer ILD1 on the peripheral circuit region PCR may include a flat portion ILD1*b* and protruding portions ILD1*a*, which protrude above the flat portion ILD1*b*. The protruding portions ILD1*a* may vertically correspond to the peripheral structure. For example, in a plan view, the protruding portions ILD1*a* of the lower insulating layer ILD1 may overlap not only the peripheral gate stacks PGS, but also the protruding portions DSPa of the dummy sacrificial pattern DSP. The protruding portions ILD1*a* of the lower insulating layer ILD1 may have a thickness T1, the flat portion ILD1*b* of the lower insulating layer ILD1 may have a thickness T2, the lower insulating layer ILD1 on the cell array regions CAR may have a thickness T3, and the lower insulating layer ILD1 on the connection regions CNR may have a thickness T4. In some embodiments, the thicknesses T1, T2, T3, and T4 may be substantially the same because the lower insulating layer ILD1 is conformally formed on the dummy sacrificial pattern DSP and the lower conductive patterns 110*a*.

The lower insulating layer ILD1 may include a material having an etch selectivity with respect to the dummy sacrificial pattern DSP. For example, the lower insulating layer ILD1 may include a silicon oxide layer, which may be formed by a deposition process having a predetermined or significant step coverage property. The lower insulating layer ILD1 may include, for example, a silicon oxide layer, which may be formed using a high density plasma chemical vapor deposition (HDP CVD) process.

Stacks ST may be provided on the lower insulating layer ILD1 and on the cell array regions CAR. Each stack ST may include upper conductive patterns 110*b* and insulating patterns 120, which are alternately and repeatedly stacked on the substrate 100. As illustrated in FIG. 3, in a plan view, the stacks ST may correspond to the lower conductive patterns 110*a*. Accordingly, on each cell array region CAR, the stacks ST may be spaced apart from each other in the second direction D2. In a plan view, each stack ST may extend from the cell array region CAR to the connection region CNR adjacent thereto, but not to the peripheral circuit region PCR. On the connection regions CNR, each stack ST may have a staircase structure with a width in the first direction D1 that stepwise increases in a downward direction. Accordingly, when viewed in a plan view, each of the upper conductive patterns 110*b*, except for the uppermost ones of the upper conductive patterns 110*b*, may include a pad portion that is exposed by the upper conductive pattern 110*b* thereon. In a plan view, each of the lower conductive patterns 110*b* may include a pad portion exposed by the stack ST thereon.

The thickness T1, T2, T3, or T4 of the lower insulating layer ILD1 may be higher than a thickness of each of the upper conductive patterns 110*b*. For example, the thickness T1, T2, T3, or T4 of the lower insulating layer ILD1 may be higher than three times the thickness of each of the upper conductive patterns 110*b*. In addition, the thickness T1, T2, T3, or T4 of the lower insulating layer ILD1 may be higher than a thickness of each of the insulating patterns 120. For example, the thickness T1, T2, T3, or T4 of the lower insulating layer ILD1 may be higher than three times the thickness of each insulating pattern 120.

At least one of the protruding portions ILD1*a* has a top surface at a level higher than a top surface of the lowermost one of the upper conductive patterns 110*b*. In addition, at least one of the protruding portions ILD1*a* has a top surface at a level higher than a top surface of the lowermost one of the insulating patterns 120.

In each stack ST, the uppermost and next-uppermost ones of the upper conductive patterns 110*b* may be used as the first and second string selection lines SSL1 and SSL2 of FIG. 2. Other or remaining ones of the upper conductive patterns 110*b* may be used as the word lines WL0-WLn of FIG. 2.

The upper conductive patterns 110*b* may be formed of or include at least one of metals (e.g., W, Al, Ti, Ta, Co, and Cu) or metal nitrides (e.g., TiN, TaN, and WN). The insulating patterns 120 may include a material having an etch selectivity with respect to the dummy sacrificial pattern DSP. For example, the insulating patterns 120 may be formed of or include silicon oxide.

An insulating separation layer 130 may be in an upper portion of each of the stacks ST. In each stack ST, the insulating separation layer 130 may cut the uppermost and next-uppermost ones of the upper conductive patterns 110*b* in the second direction D2. The insulating separation layer 130 may be formed of or include, for example, silicon oxide.

Common source regions CSR may be in the cell array regions CAR and between the stacks ST spaced apart from each other in the second direction D2. Accordingly, each of the common source regions CSR may extend in the first direction D1 and may include a portion in the connection region CNR. The common source regions CSR may be parts of the substrate 100, which are doped to have a second conductivity type (e.g., n-type) different from the first conductivity type.

Common source plugs CSP may be on and coupled to the common source regions CSR, respectively. Each common source plug CSP may extend in the first direction D1. The common source plugs CSP may be formed of or include, for example, at least one of metals (e.g., W, Cu, Al, Ti, or Ta).

Insulating spacers SP may be between the common source plugs CSP and the stacks ST and may be used to electrically separate the common source plugs CSP from the upper conductive patterns 110b. The insulating spacers SP may be formed of or include, for example, silicon oxide, silicon nitride, or silicon oxynitride.

An upper insulating layer ILD2 may be on the peripheral circuit region PCR and the connection regions CNR to cover the lower insulating layer ILD1 and the stacks ST. On the peripheral circuit region PCR, the upper insulating layer ILD2 may be directly on the lower insulating layer ILD1. For example, on the peripheral circuit region PCR, the upper insulating layer ILD2 may be in contact with the lower insulating layer ILD1. On the peripheral circuit region PCR, the upper insulating layer ILD2 may cover the protruding portions ILD1a of the lower insulating layer ILD1. The upper insulating layer ILD2 may be on the connection regions CNR to cover the staircase portions of the stacks ST. The upper insulating layer ILD2 may have a flat top surface.

The upper insulating layer ILD2 may be at a deposition rate higher than that of the lower insulating layer ILD1. For example, the upper insulating layer ILD2 may be formed by a deposition technique which may realize a higher deposition rate than that of the deposition technique (e.g., HDP CVD) for the lower insulating layer ILD1. For example, the upper insulating layer ILD2 may include a tetraethyl orthosilicate (TEOS) layer, which is formed by a plasma-enhanced chemical vapor deposition (PE-CVD) process. In this case, lower and upper insulating layers ILD1 and ILD2 may contain silicon oxide, but the density of the upper insulating layer ILD2 may be lower than that of lower insulating layer ILD1.

A first interlayered insulating layer 140 may cover the resulting structure including the stacks ST and the upper insulating layer ILD2. The first interlayered insulating layer 140 may be on all of the peripheral circuit region PCR, the connection regions CNR, and the cell array regions CAR to cover the stacks ST and the upper insulating layer ILD2. The first interlayered insulating layer 140 may be formed of or include, for example, silicon oxide, silicon nitride, or silicon oxynitride. In some embodiments, the first interlayered insulating layer 140 may be omitted.

Vertical structures VS may be on the cell array regions CAR. Each of the vertical structures VS may be provided to sequentially penetrate the first interlayered insulating layer 140, the stack ST, the lower insulating layer ILD1, the lower conductive pattern 110a, and the buffer insulating layer 105.

In a plan view, the vertical structures VS may be arranged in a line or in a predetermined pattern, e.g., a zigzag pattern. For example, as shown in FIG. 3, the vertical structures VS in each stack ST may be arranged to form nine columns, each of which is parallel to the first direction D1. In such an example, the vertical structures VS of the fifth column may not be connected to a bit line BL as described below, and the vertical structures VS of other columns may be connected to the bit line BL.

Each of the vertical structures VS may include a lower semiconductor pattern LSP, an upper semiconductor pattern USP, an insulating filler pattern VI, a vertical insulating pattern VP, and a conductive pad CP. The lower semiconductor pattern LSP may be used as a lower portion of the vertical structure VS and may be in contact with the substrate 100. The lower semiconductor pattern LSP may have a predetermined (e.g., pillar-shaped) structure extending in a third direction D3 normal to the top surface of the substrate 100. The lower semiconductor pattern LSP may penetrate the lower conductive pattern 110a. In certain embodiments, the lower semiconductor pattern LSP may be inserted into the top surface of the substrate 100 or in a recess region 100r. The lower semiconductor pattern LSP may have a top surface higher than a bottom surface of the lower insulating layer ILD1 and lower than a top surface of the flat portion ILD1b. The lower semiconductor pattern LSP may be formed, for example, by a selective epitaxial growth process using the substrate 100 as a seed layer and may include silicon. The lower semiconductor pattern LSP may have the same conductivity type as the substrate 100.

A gate insulating layer GOX may be between side surfaces of the lower semiconductor pattern LSP and the lower conductive pattern 110a. The gate insulating layer GOX may be formed of or include, for example, silicon oxide.

The upper semiconductor pattern USP may be on the lower semiconductor pattern LSP. The upper semiconductor pattern USP may extend in the third direction D3. The upper semiconductor pattern USP may include a lower portion, which is electrically connected to the lower semiconductor pattern LSP, and an upper portion which is electrically connected to the bit line BL.

The upper semiconductor pattern USP may have a predetermined shape, e.g., a hollow pipe or a macaroni noodle. The upper semiconductor pattern USP may have a bottom in a closed state. An inner space of the upper semiconductor pattern USP may be filled with the insulating filler pattern VI. A bottom surface of the upper semiconductor pattern USP may be at a level lower than the topmost surface of the lower semiconductor pattern LSP.

In some embodiments (e.g., as illustrated in FIG. 5), the upper semiconductor pattern USP may include a first semiconductor pattern SP1 and a second semiconductor pattern SP2. The first semiconductor pattern SP1 may be coupled to the lower semiconductor pattern LSP and may have a predetermined shape, e.g. a bottom-closed pipe or a macaroni noodle. An inner space of the first semiconductor pattern SP1 may be filled with the insulating filler pattern VI. The first semiconductor pattern SP1 may be partially inserted into the lower semiconductor pattern LSP. The first semiconductor pattern SP1 may be in contact with an inner side surface of the second semiconductor pattern SP2 and the top surface of the lower semiconductor pattern LSP. Accordingly, the first semiconductor pattern SP1 may be used to electrically connect the second semiconductor pattern SP2 to the lower semiconductor pattern LSP. The second semiconductor pattern SP2 may have a predetermined shape (e.g., a hollow pipe or macaroni noodle) with an open top and bottom. The second semiconductor pattern SP2 may be spaced apart from (e.g., not in contact with) the lower semiconductor pattern LSP.

The upper semiconductor pattern USP may be in an undoped state or may be doped to have the same conductivity type as the substrate 100. The upper semiconductor pattern USP may be formed of or include at least one of doped or intrinsic semiconductor materials (e.g., of silicon (Si), germanium (Ge), or compounds thereof).

The conductive pads CP may be on respective ones of the upper semiconductor patterns USP. The conductive pads CP may include at least one of doped semiconductor materials or metallic materials. The vertical insulating pattern VP may be between the upper semiconductor pattern USP and the upper conductive patterns 110b. The vertical insulating pattern VP may include a blocking insulating layer, adjacent to the upper conductive patterns 110b, a tunnel insulating layer, adjacent to the upper semiconductor pattern USP, and a charge storing layer therebetween. The tunnel insulating layer may be formed of or include, for example, a silicon oxide layer. The charge storing layer may be formed of or include, for example, a silicon nitride layer, a silicon oxynitride layer, a silicon-rich nitride layer, an insulating layer with conductive nanodots, or a laminated trap layer. The blocking insulating layer may be formed of or include at least one of a silicon oxide layer, a silicon nitride layer, a silicon oxynitride layer, or metal oxide layers.

A lower horizontal insulating pattern 112a may be between the gate insulating layer GOX and each of the lower conductive patterns 110a. The lower horizontal insulating pattern 112a may extend to cover top and bottom surfaces of the lower conductive pattern 110a. The lower horizontal insulating pattern 112a may be formed of or include, for example, silicon oxide, metal oxide, or metal nitride.

An upper horizontal insulating pattern 112b may be between each pair of the vertical structure VS and the upper conductive pattern 110b. The upper horizontal insulating pattern 112b may cover top and bottom surfaces of each of the upper conductive patterns 110b. The upper horizontal insulating pattern 112b may be formed of or include, for example, silicon oxide, metal oxide, or metal nitride.

In addition, dummy vertical structures DVS may be on the connection region CNR. Each of the dummy vertical structures DVS may have substantially the same structural features as the vertical structure VS. The dummy vertical structures DVS may penetrate end portions of the upper and lower conductive patterns 110b and 110a.

A second interlayered insulating layer 142 may be on the first interlayered insulating layer 140. The second interlayered insulating layer 142 may cover the vertical structures VS and the common source plugs CSP. The second interlayered insulating layer 142 may be formed of or include, for example, silicon oxide, silicon nitride, or silicon oxynitride.

Contact plugs PLG may be on the cell array regions CAR, may penetrate the second interlayered insulating layer 142, and may be coupled to the vertical structures VS, respectively.

Cell contact plugs CPLG may be on the connection regions CNR. Each cell contact plugs CPLG may penetrate the first and second interlayered insulating layers 140 and 142 and the upper insulating layer ILD2 and may be coupled to a corresponding one of the lower and upper conductive patterns 110a and 110b. Some of the cell contact plugs CPLG, which are connected to the lower conductive patterns 110a, may further penetrate the lower insulating layer ILD1.

Peripheral contact plugs PPLG may be on the peripheral circuit region PCR, may penetrate the first and second interlayered insulating layers 140 and 142, the lower and upper insulating layers ILD1 and ILD2, and the dummy sacrificial pattern DSP, and may be coupled to the peripheral structure. The peripheral contact plugs PPLG may penetrate the protruding portion ILD1a of the lower insulating layer ILD1. The peripheral contact plugs PPLG may be coupled, for example, to the source/drain regions SD and/or the peripheral gate stacks PGS.

Sub-bit lines SBL may be on the cell array regions CAR and on the second interlayered insulating layer 142. In some embodiments, each sub-bit line SBL may be coupled to a pair of the contact plugs PLG. For example, each sub-bit line SBL may be electrically connected to an adjacent pair of the vertical structures VS, between which the insulating separation layer 130 or the common source plug CSP is interposed.

Connection lines CL may be on the connection regions CNR and on the second interlayered insulating layer 142. The connection lines CL may be coupled to the cell contact plugs CPLG.

Peripheral circuit lines PCL may be on the peripheral circuit region PCR and on the second interlayered insulating layer 142. The peripheral circuit lines PCL may be coupled to the peripheral contact plugs PPLG.

A third interlayered insulating layer 144 may be on the second interlayered insulating layer 142. The third interlayered insulating layer 144 may cover the sub-bit lines SBL, the connection lines CL, and the peripheral circuit lines PCL. The third interlayered insulating layer 144 may be formed of or include, for example, silicon oxide, silicon nitride, or silicon oxynitride.

Bit lines BL may be on the third interlayered insulating layer 144, may cross the stacks ST or extend in the second direction D2, and may be coupled to the sub-bit lines SBL through bit line contact plugs BPLG.

In a semiconductor device according to some embodiments, the stacks ST and the vertical structures VS may be formed on the lower insulating layer ILD1, on which a planarization process is not performed. Accordingly, it may be possible to prevent defects (e.g., scratch) from being formed on the top surface of the lower insulating layer ILD1 by a planarization process. Thus, it may be possible to improve reliability of the semiconductor device. Here, the protruding portions ILD1a of the lower insulating layer ILD1 can exist because the planarization process on the lower insulating layer ILD1 is omitted.

Figure 6B:
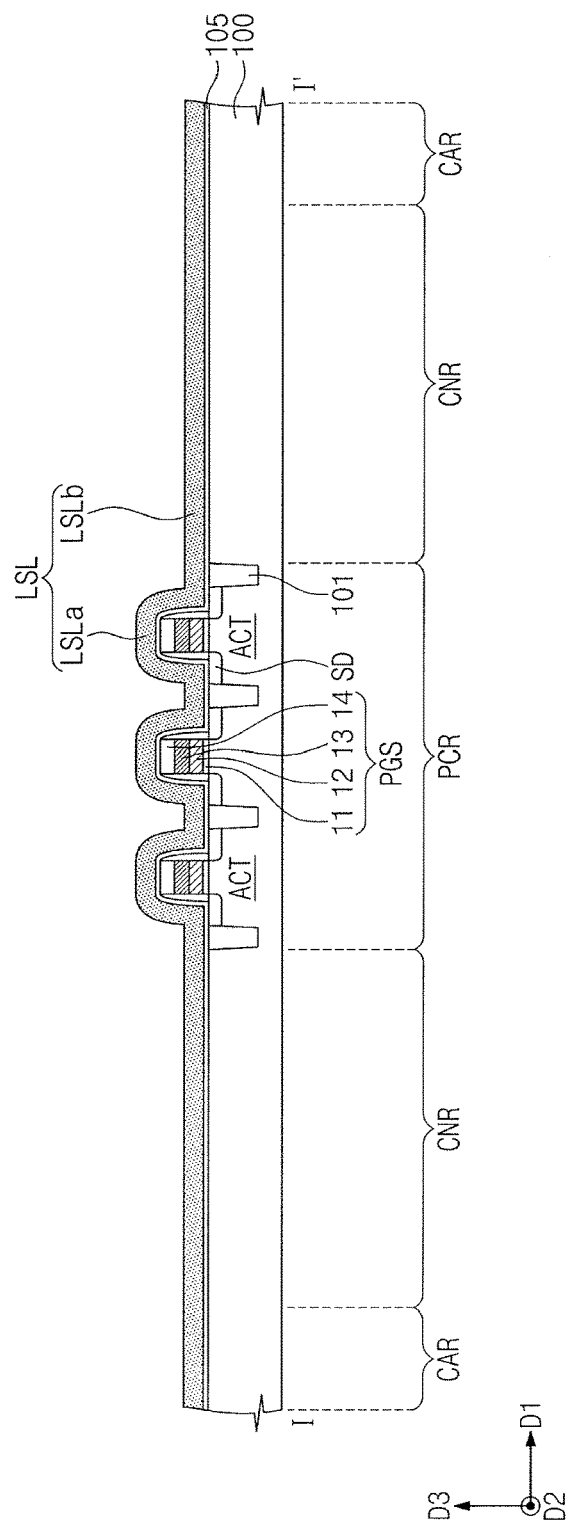
FIGS. 6A-6N illustrate various stages of an embodiment of a method for fabricating a three-dimensional semiconductor device in FIG. 3 along one section line.
Figure 6C:
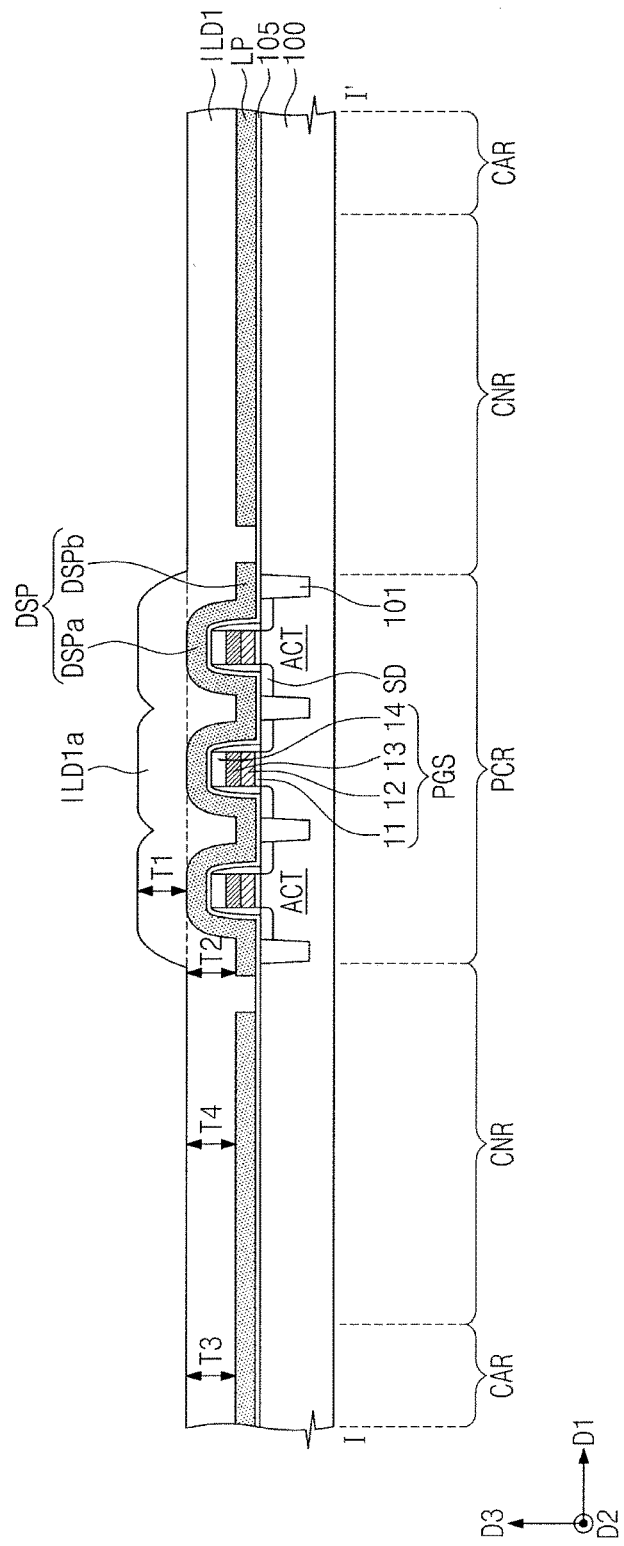
Figure 6D:
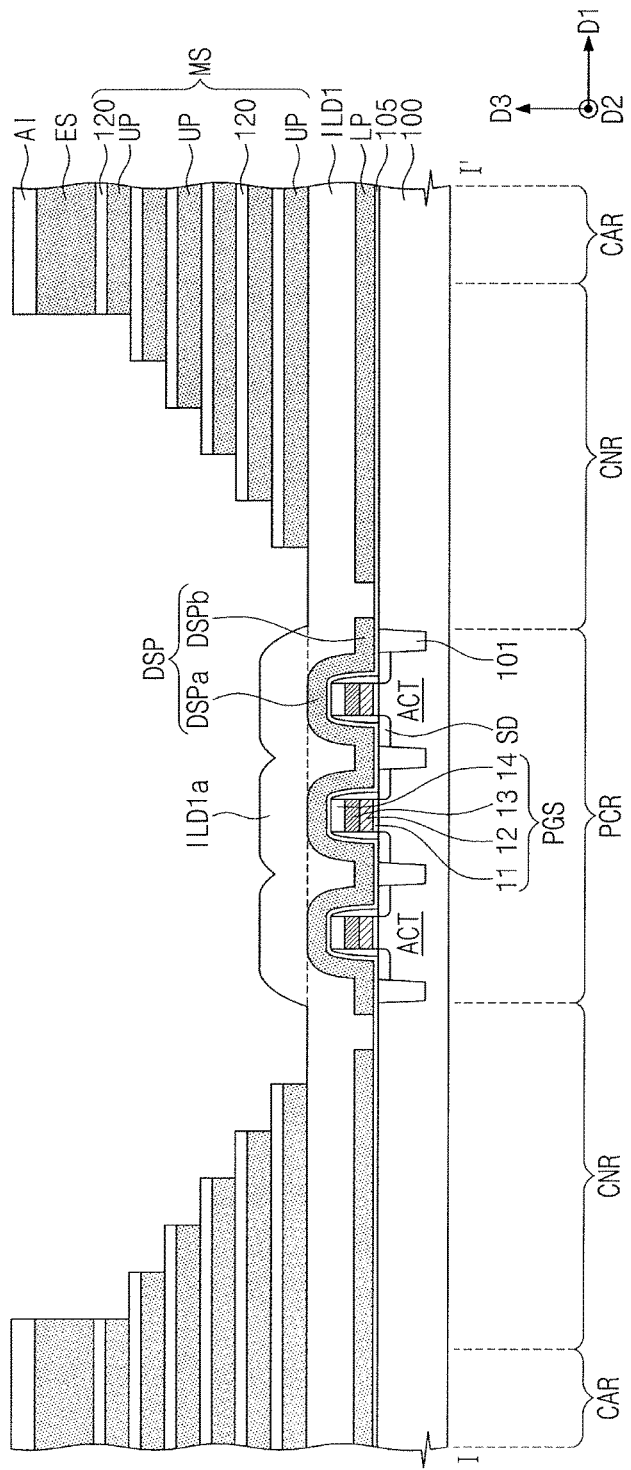
Figure 6E:
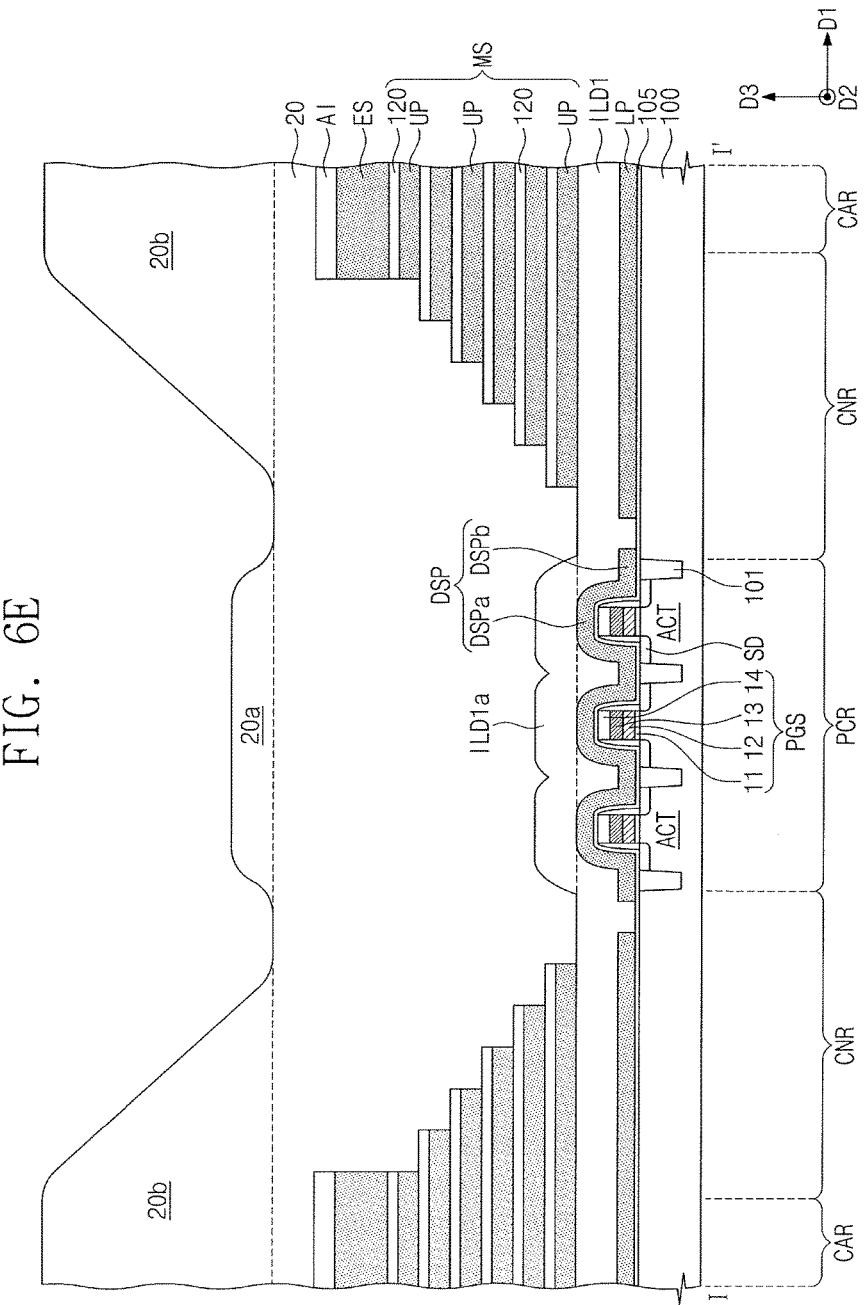
Figure 6F:
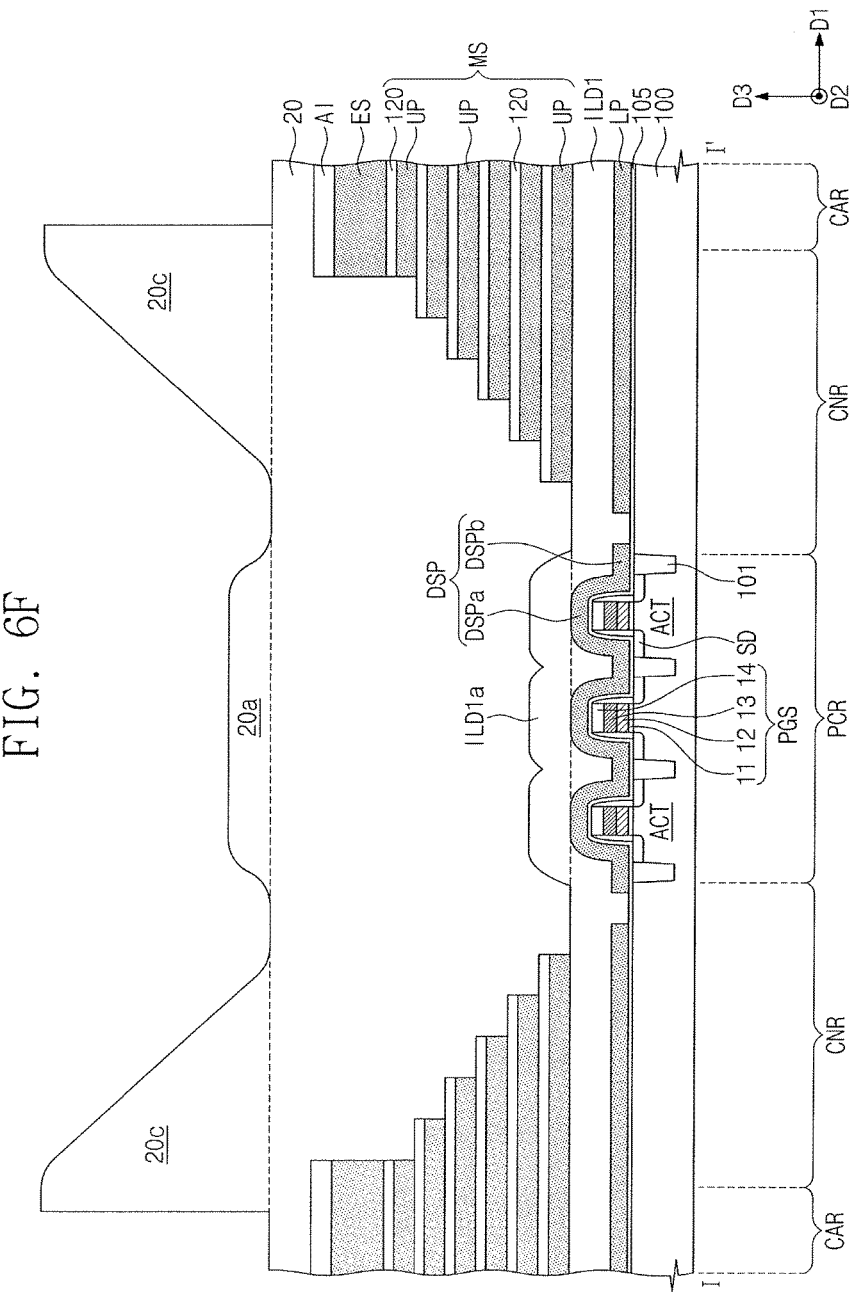
Figure 6G:
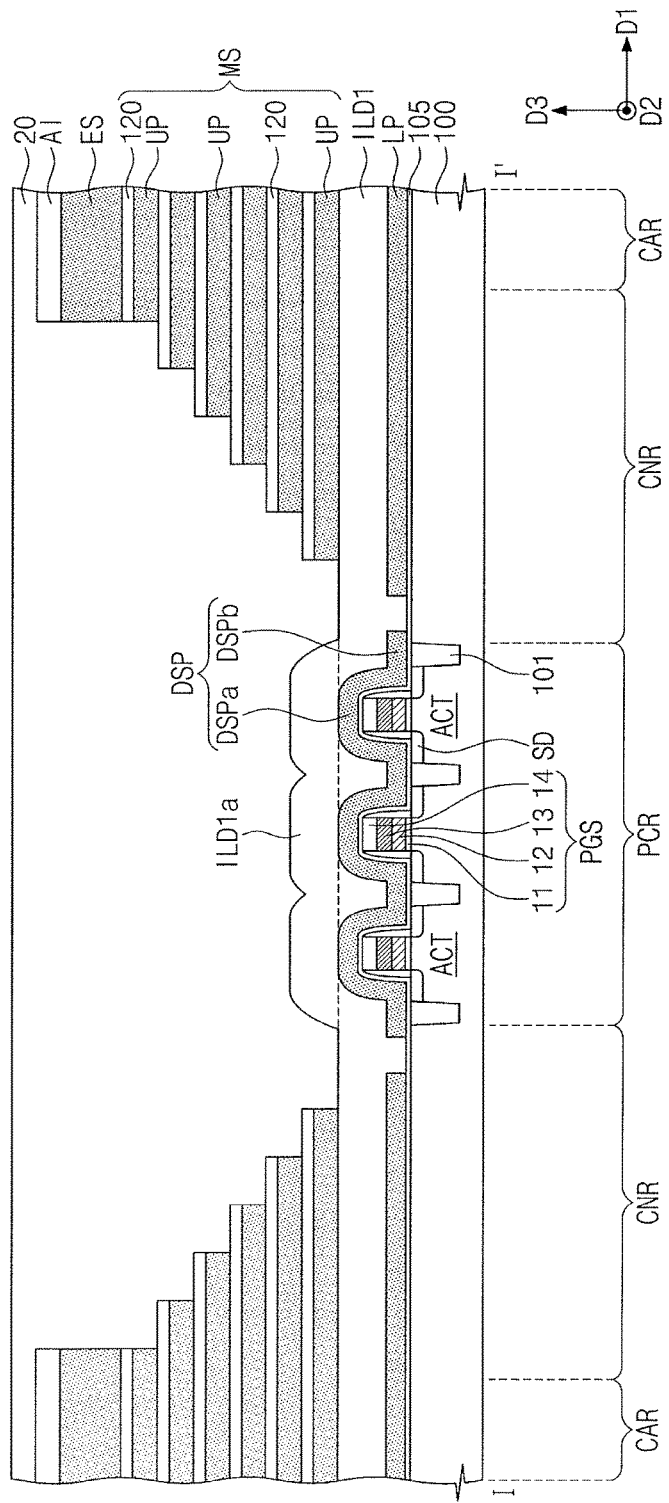
Figure 6H:
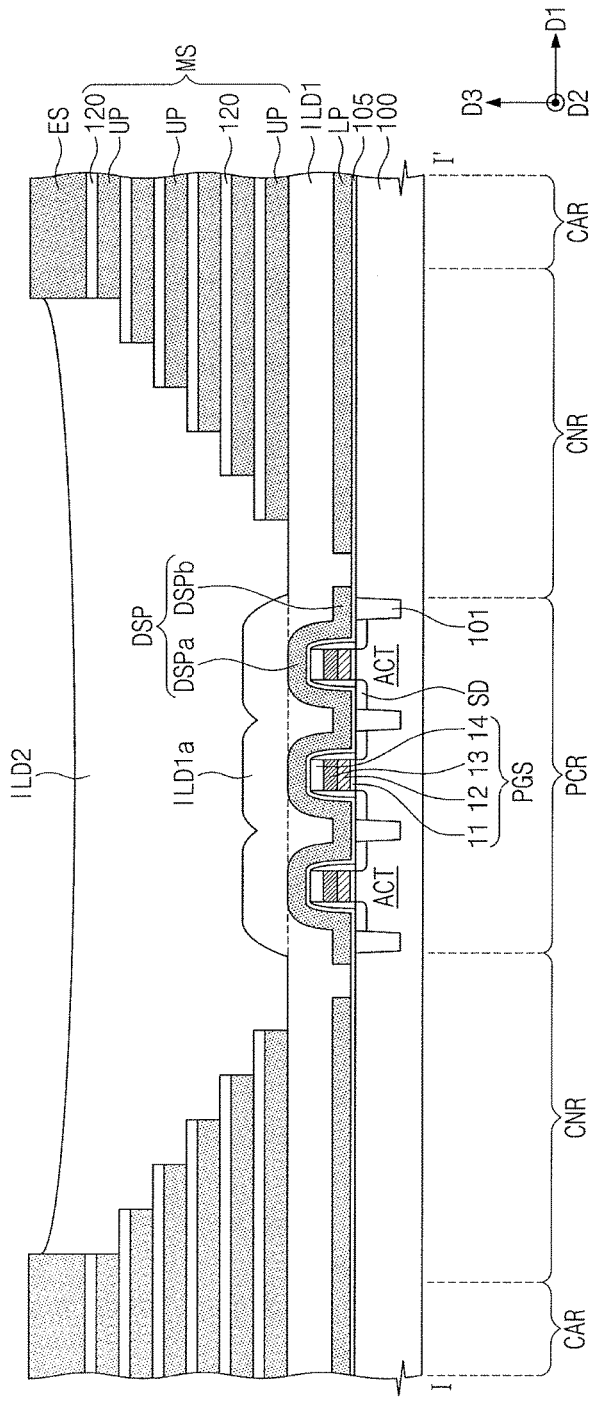
Figure 6I:
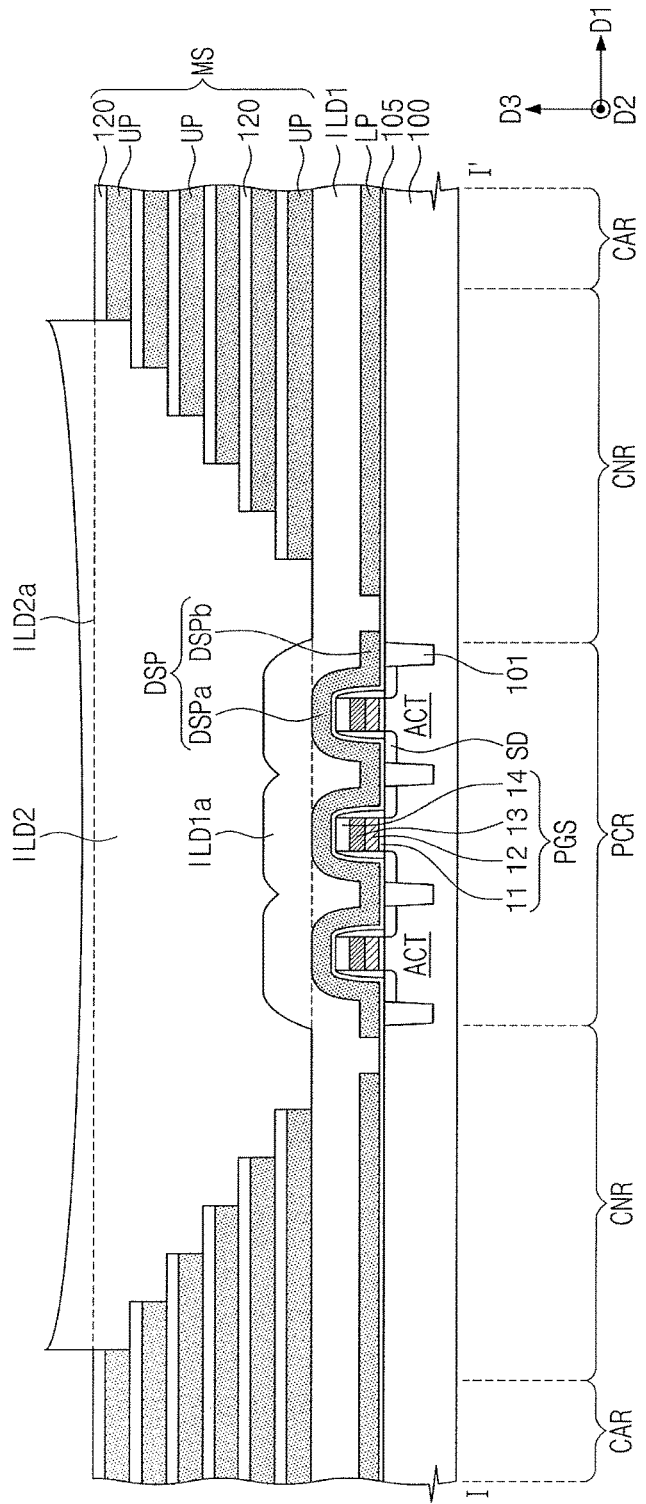
Figure 6J:
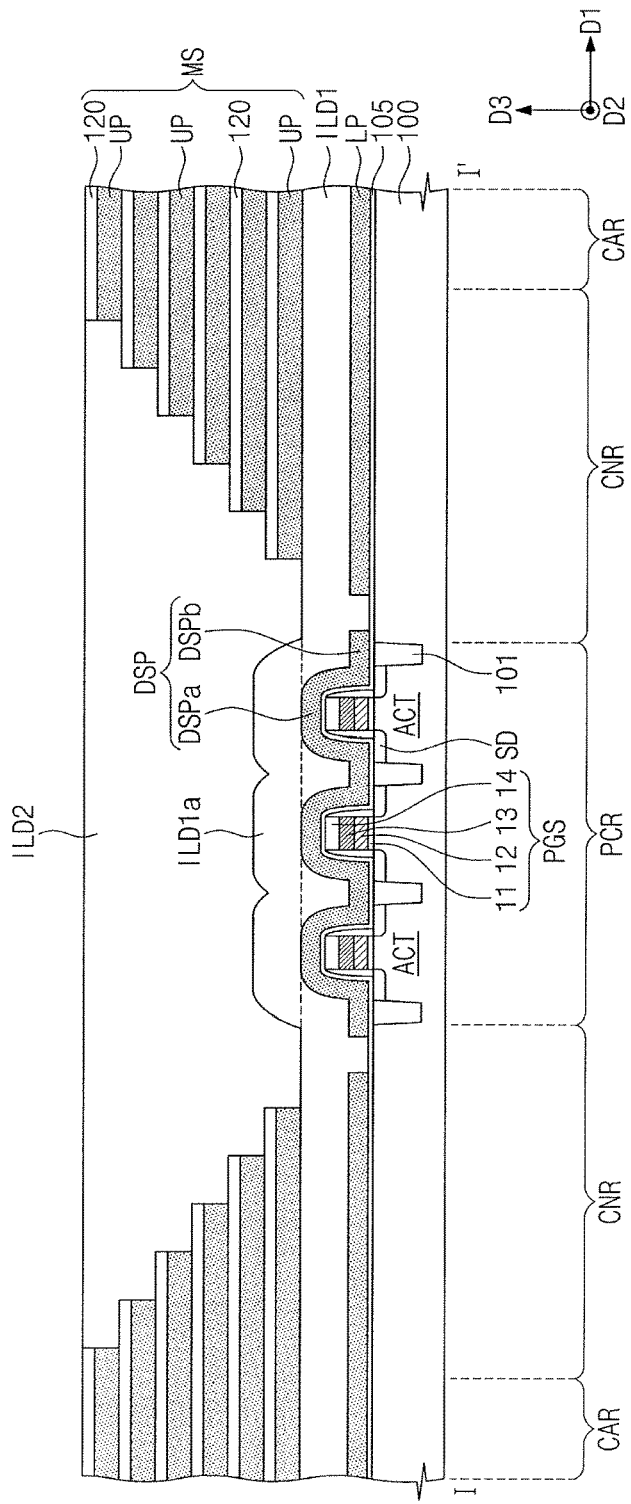
Figure 6K:
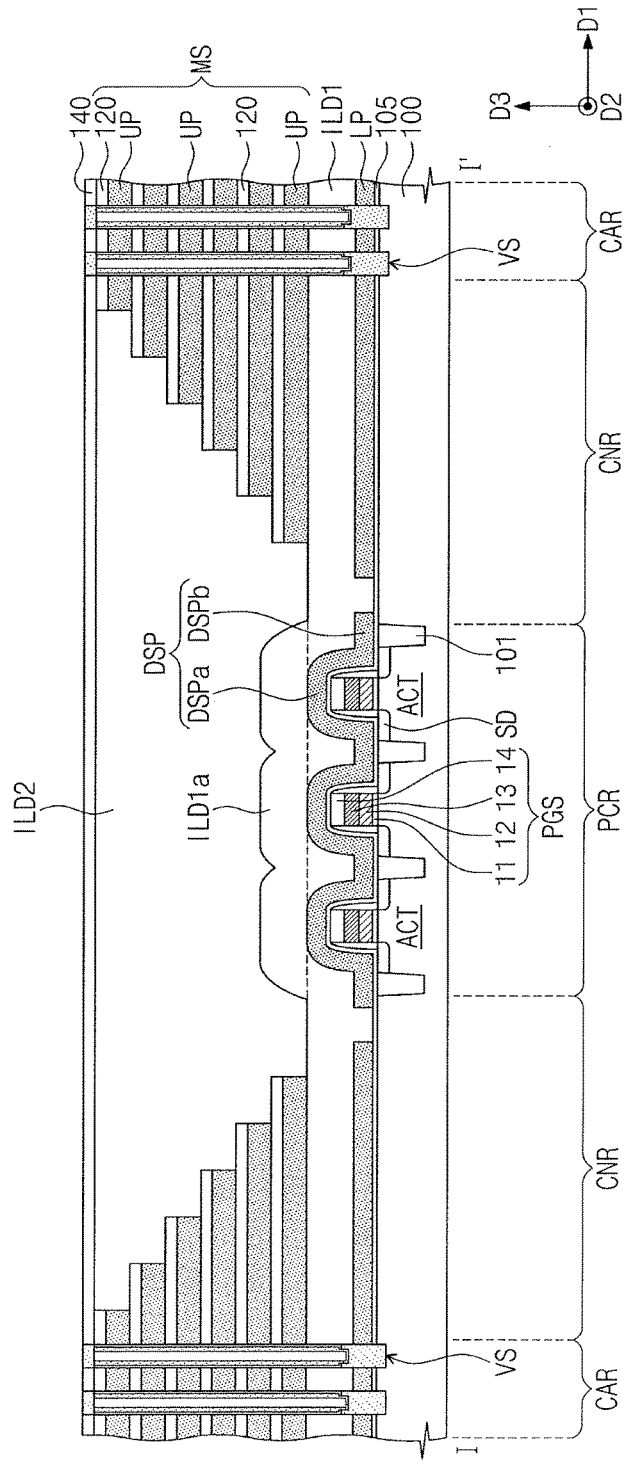
Figure 6L:
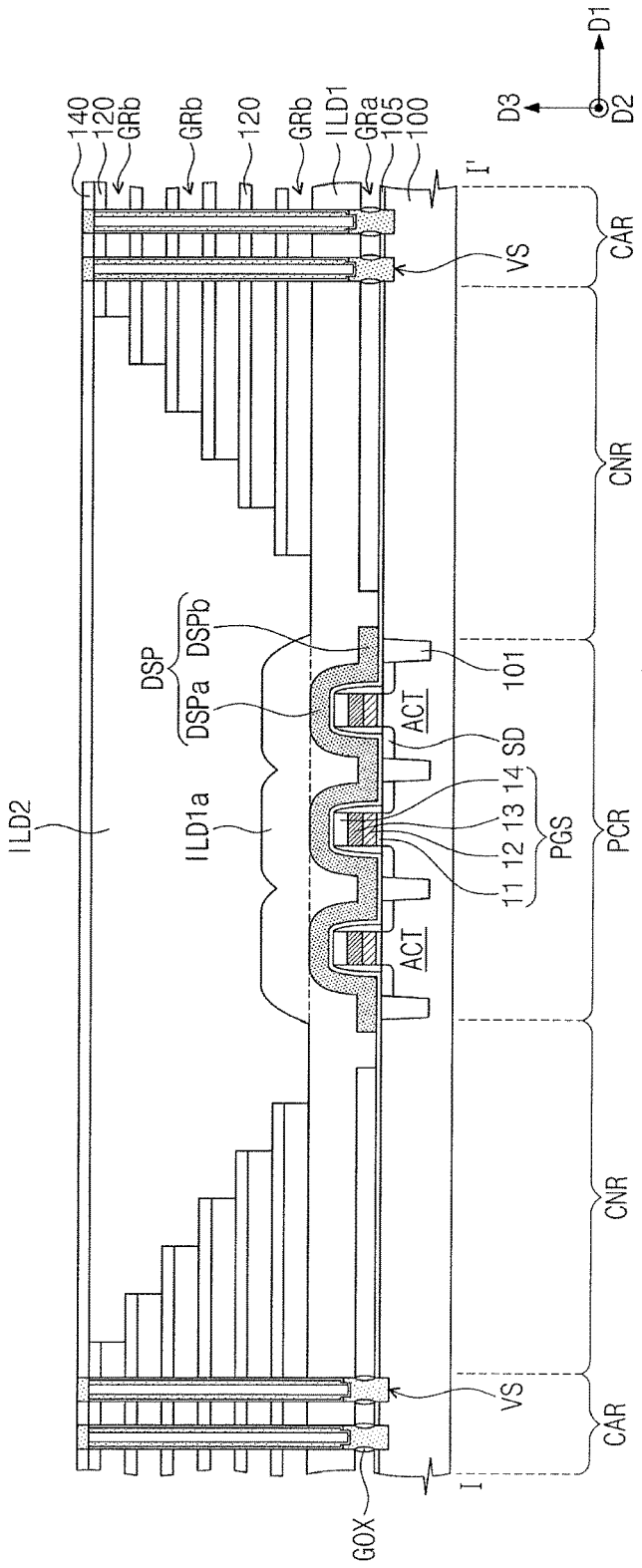
Figure 6M:
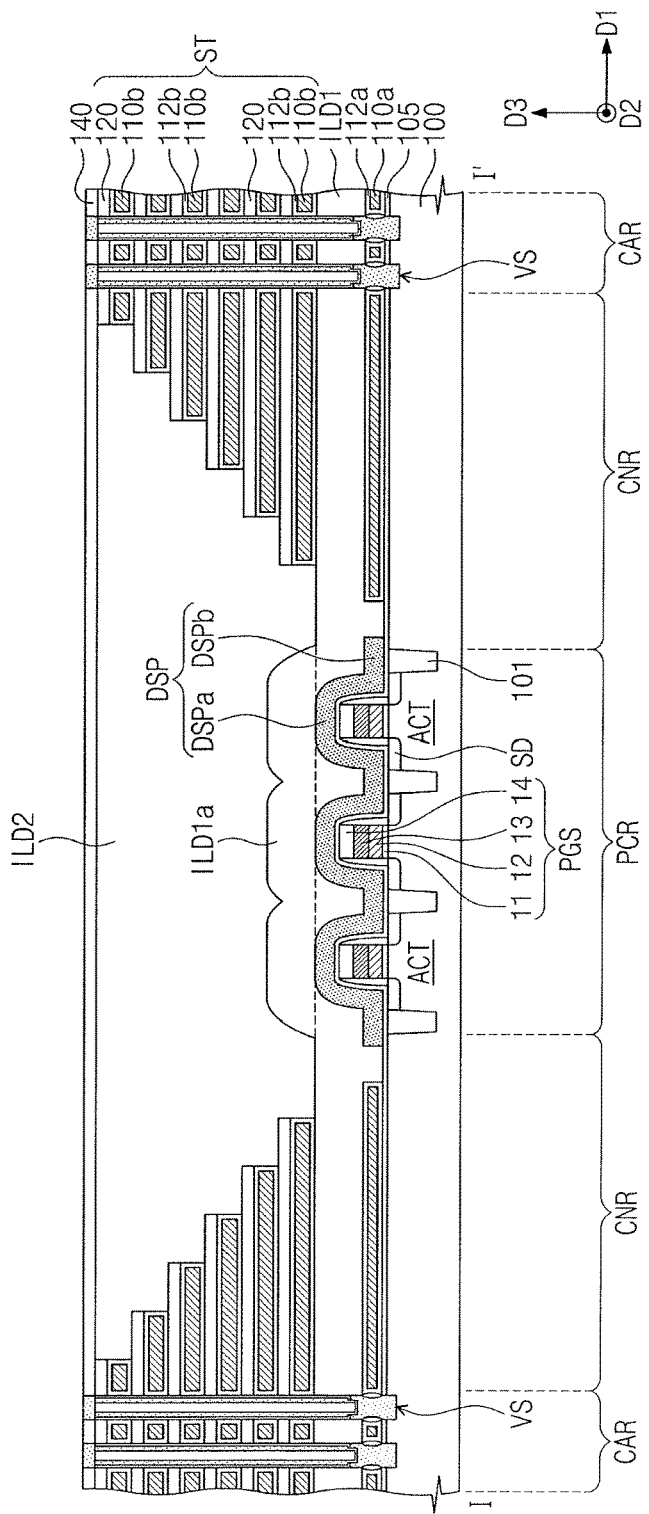
Figure 6N:
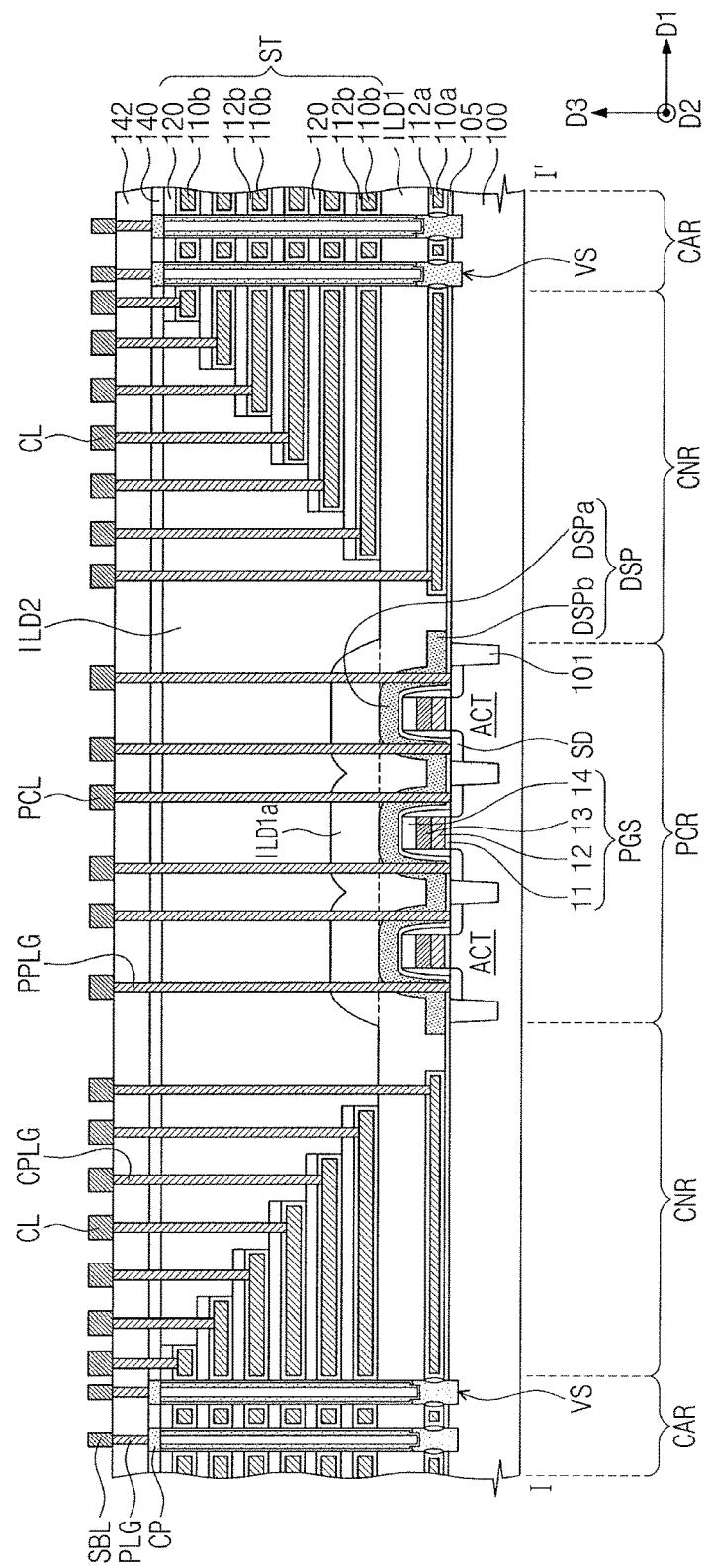
Figure 7A:
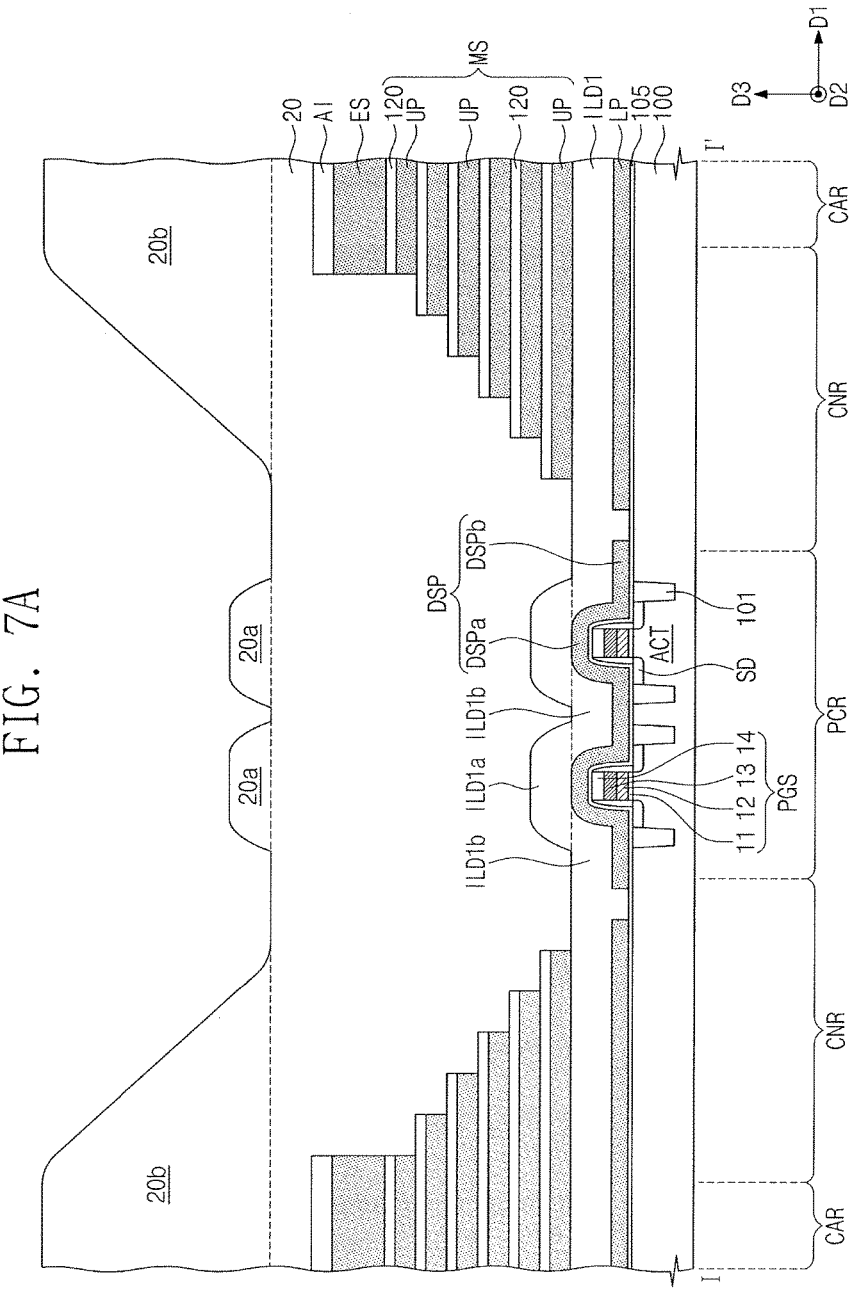
FIGS. 7A-7C illustrate are sectional views taken along another section line in FIG. 3.
Figure 7B:
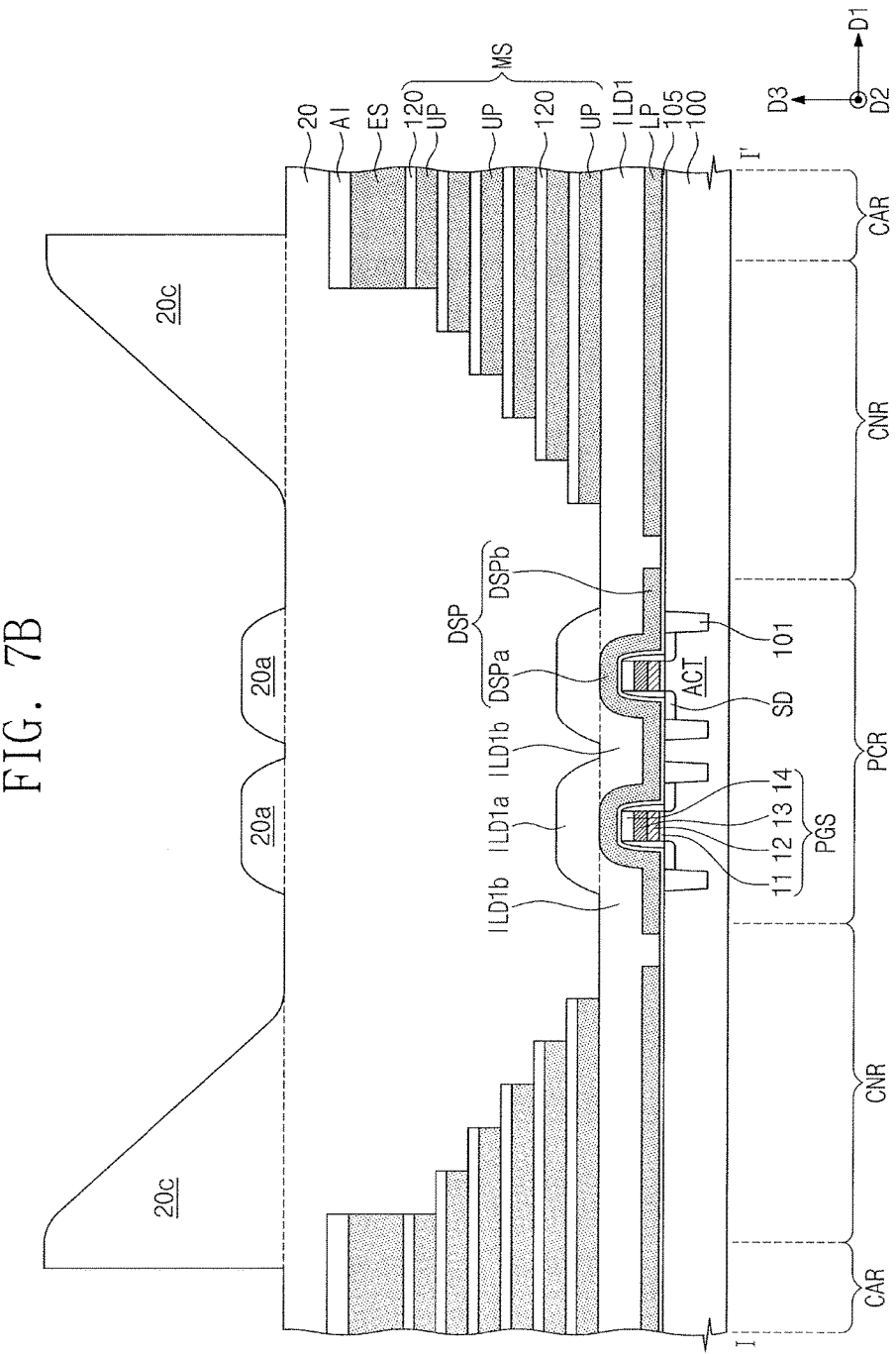
Figure 7C:
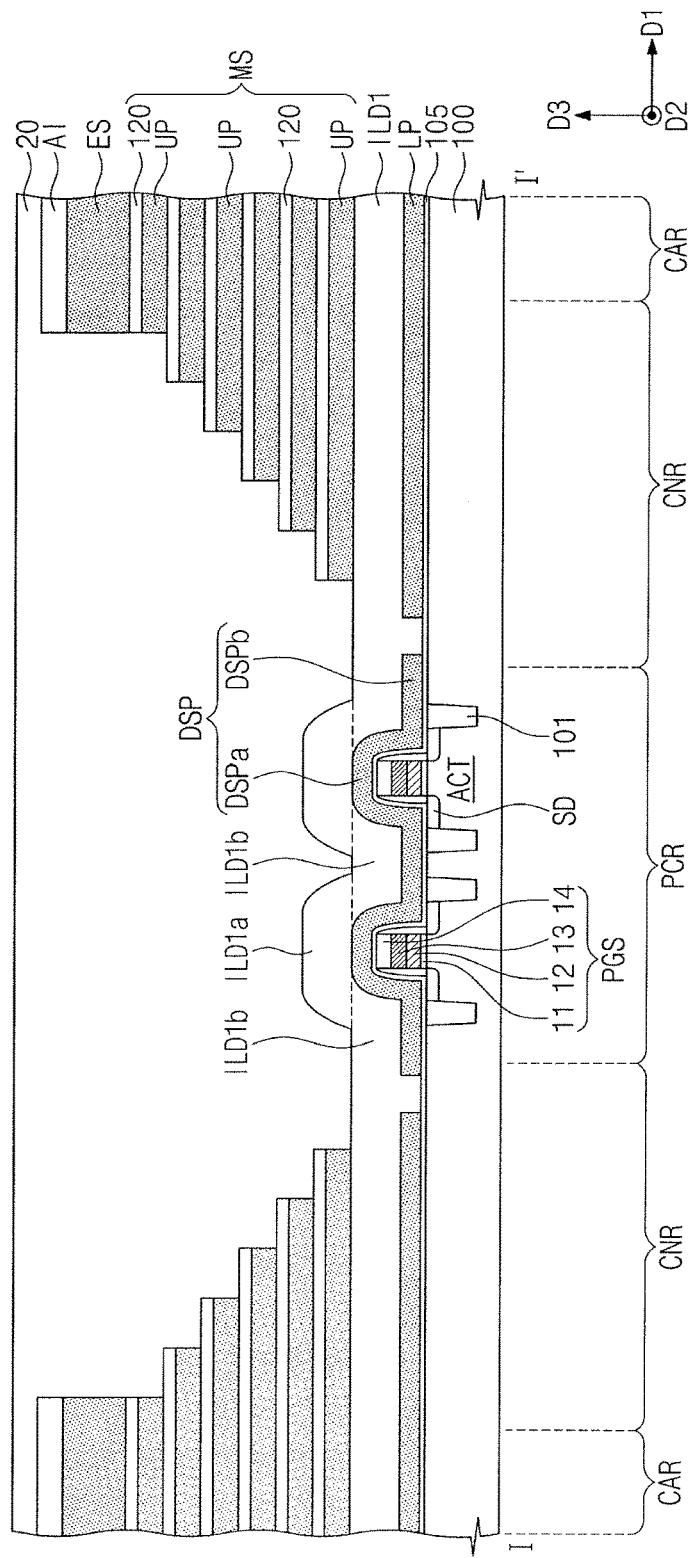

FIGS. 6A-6N are sectional views illustrating various stages of an embodiment of a method for fabricating a three-dimensional semiconductor device. For example, FIGS. 6A-6N are sectional views corresponding to line I-I' of FIG. 3. FIGS. 7A-7C are sectional views corresponding to line II-II' of FIG. 3. FIGS. 8A to 8G are sectional views corresponding to line III-III' of FIG. 3.

Referring to FIGS. 3 and 6A, the substrate 100 is provided with the cell array regions CAR, the peripheral circuit region PCR, and the connection regions CNR. The cell array regions CAR may be spaced apart from each other in the first direction D1. The peripheral circuit region PCR may be between the cell array regions CAR. Each of the connection regions CNR may be between a corresponding one of the cell array regions CAR and the peripheral circuit region PCR. For example, the substrate 100 may be a silicon wafer of a first conductivity type (e.g., p-type).

The peripheral structure may be on the peripheral circuit region PCR and may have substantially the same features as that described with reference to FIGS. 3 and 4A to 4C. For example, the peripheral structure may include the peripheral gate stacks PGS which are on the peripheral circuit region PCR and which are spaced apart from each other.

Referring to FIGS. 3 and 6B, the buffer insulating layer 105 and a lower sacrificial layer LSL may be sequentially formed to cover the resulting structure with the peripheral structure. The buffer insulating layer 105 may be formed to conformally cover the peripheral gate stacks PGS on the peripheral circuit region PCR and to cover the connection regions CNR and the cell array regions CAR.

The lower sacrificial layer LSL may be conformally formed on the buffer insulating layer 105. Accordingly, the lower sacrificial layer LSL may include protruding portions LSLa formed on the peripheral gate stacks PGS and an extended portion LSLb overlapping the substrate 100 but not the peripheral gate stacks PGS. The lower sacrificial layer LSL may include a material having an etch selectivity with respect to the buffer insulating layer 105. For example, the lower sacrificial layer LSL may be formed of or include silicon nitride or silicon oxynitride.

Referring to FIGS. 3 and 6C, the lower sacrificial layer LSL may be patterned to form lower sacrificial patterns LP and sacrificial patterns DSP, which are spaced apart from each other. Formation of the lower and dummy sacrificial patterns LP and DSP may include forming a mask pattern on the lower sacrificial layer LSL to define openings on the peripheral circuit region PCR or the connection regions CNR and anisotropically etching the lower sacrificial layer LSL using the mask pattern as an etch mask. The openings of the mask pattern may be spaced apart from the peripheral gate stacks PGS.

The dummy sacrificial pattern DSP may include the protruding portions DSPa provided on the peripheral gate stacks PGS and the extended portion DSPb overlapping the peripheral circuit region PCR but not the peripheral gate stacks PGS. The lower sacrificial patterns LP may cover the buffer insulating layer 105 on the cell array regions CAR and the connection regions CNR.

The lower insulating layer ILD1 may be formed to cover the resulting structure with the lower sacrificial patterns LP and the dummy sacrificial pattern DSP. The lower insulating layer ILD1 may formed of or include a material having an etch selectivity with respect to the dummy sacrificial pattern DSP. For example, the lower insulating layer ILD1 may be formed of or include silicon oxide.

The lower insulating layer ILD1 may be formed to have a predetermined or significant step coverage property. The lower insulating layer ILD1 may be formed by, for example, a high density plasma chemical vapor deposition (HDP CVD) process.

On the peripheral circuit region PCR, the lower insulating layer ILD1 may have a flat portion (e.g., ILD1b of FIG. 4B) and the protruding portions ILD1a protruding above the flat portion ILD1b. The protruding portions ILD1a may vertically correspond to the peripheral structure. For example, in a plan view, the protruding portions ILD1a of the lower insulating layer ILD1 may be overlapped not only with the peripheral gate stacks PGS but also with the protruding portions DSPa of the dummy sacrificial pattern DSP. The lower insulating layer ILD1 may be deposited on the lower sacrificial patterns LP and the dummy sacrificial pattern DSP with a uniform or predetermined thickness. Referring to FIGS. 4B and 6C, the protruding portions ILD1a of the lower insulating layer ILD1 may have a thickness T1, the flat portion ILD1b of the lower insulating layer ILD1 may have a thickness T2, the lower insulating layer ILD1 on the cell array regions CAR may have a thickness T3, and the lower insulating layer ILD1 on the connection regions CNR may have a thickness T4. In some embodiments, the thicknesses T1, T2, T3, and T4 may be substantially the same.

Referring to FIGS. 3 and 6D, a mold structure MS may be formed on each of the cell array regions CAR. The mold structure MS may be formed on the lower insulating layer ILD1 and may include upper sacrificial patterns UP and the insulating patterns 120, which are alternately and repeatedly stacked on the substrate 100. In a plan view, each of the mold structures MS may extend from the cell array region CAR to the connection region CNR adjacent thereto, but not to the peripheral circuit region PCR. When viewed in a plan view, the mold structure MS may be overlapped with the lower sacrificial pattern LP thereunder, but may partially expose the lower sacrificial pattern LP on the connection region CNR.

On the connection regions CNR, the mold structure MS may have a staircase structure having a width in the first direction D1 that stepwise increases in a downward direction. Accordingly, in a plan view, each of the upper sacrificial patterns UP, except for the uppermost one of the upper sacrificial patterns UP, may include a portion exposed by the upper sacrificial pattern UP thereon. The upper sacrificial patterns UP may include a material having an etch selectivity with respect to the insulating patterns 120. For example, the insulating patterns 120 may include silicon oxide and the upper sacrificial patterns UP may include silicon nitride or silicon oxynitride.

The mold structure MS may be directly or immediately formed on the lower insulating layer ILD1, without a planarization process on the lower insulating layer ILD1. Accordingly, the mold structure MS may be formed on the lower insulating layer ILD1, which does not have defects (e.g., scratch) caused by a planarization process.

The lower insulating layer ILD1 may be formed in such a way that at least one of the protruding portions ILD1a has a top surface at a level higher than a top surface of the lowermost one of the upper conductive patterns 110b of the mold structure MS. In addition, the lower insulating layer ILD1 may be formed in such a way that at least one of the protruding portions ILD1a has a top surface at a level higher than a top surface of the lowermost one of the insulating patterns 120 of the mold structure MS.

An etch stop pattern ES may be formed on the uppermost one of the insulating patterns 120 of the mold structure MS. The etch stop pattern ES may include a material having an etch selectivity with respect to an insulating gapfill layer 20. For example, the etch stop pattern ES may be formed of or include silicon nitride or silicon oxynitride. The thickness of the etch stop pattern ES may be higher than that of any of the upper sacrificial patterns UP and the insulating patterns 120. For example, the thickness of the etch stop pattern ES may be higher than three times that of any of the upper sacrificial patterns UP and the insulating patterns 120.

An additional insulating pattern AI may be formed on the etch stop pattern ES. The additional insulating pattern AI may be formed of or include, for example, silicon oxide.

Formation of the mold structure MS, the etch stop pattern ES, and the additional insulating pattern AI may include alternately and repeatedly forming upper sacrificial layers and insulating layers on the substrate 100 provided with the lower insulating layer ILD1, sequentially forming an etch stop layer and an additional insulating layer on the uppermost layer of the insulating layers, and performing a trimming process on underlying layers (e.g., the additional insulating layer, the etch stop layer, the insulating layers, and the upper sacrificial layers. Since any planarization process is not performed on the lower insulating layer ILD1, the underlying layers may be formed to cover the protruding portions ILD1a of the lower insulating layer ILD1.

The trimming process may include a plurality of trimming steps, each of which includes forming a mask pattern to cover the underlying layers on the cell array regions CAR and the connection regions CNR, etching exposed portions of the underlying layers, and reducing a horizontal area of the mask pattern.

Referring to FIGS. 3, 6E, 7A, and 8A, the insulating gapfill layer 20 may be formed on the substrate 100 provided with the mold structure MS. The insulating gapfill layer 20 may be formed directly on the lower insulating layer ILD1 to cover the protruding portions ILD1a of the lower insulating layer ILD1. In one embodiment, the insulating gapfill layer 20 may be formed to be thicker than the mold structure MS.

The insulating gapfill layer 20 may have a top surface profile corresponding to the structure of FIG. 6D. For example, the top surface of the insulating gapfill layer 20 may be inclined on the connection regions CNR and may be substantially flat on the cell array regions CAR.

The insulating gapfill layer 20 may have first protruding portions 20a on the peripheral circuit region PCR and second protruding portions 20b on the connection regions CNR and the cell array regions CAR. The first protruding portions 20a of the insulating gapfill layer 20 may result from the protruding portions ILD1a of the lower insulating layer ILD1, and thus may respectively overlap the protruding portions ILD1a of the lower insulating layer ILD1 in a plan view. The second protruding portions 20b of the insulating gapfill layer 20 may result from the mold structures MS, and thus may respectively overlap the mold structures MS in a plan view.

The shape of the first protruding portion 20a may be different in other embodiments, for example, depending on the space between the protruding portions ILD1a or between the peripheral gate stacks PGS.

In some embodiments, as illustrated in FIG. 6E, at least two portions of the insulating gapfill layer 20 corresponding to adjacent ones of the protruding portions ILD1a may be united to form a single first protruding portion 20a. In this case, the single first protruding portion 20a may overlap a plurality of the protruding portions ILD1a of the lower insulating layer ILD1 in a plan view.

In certain embodiments, as illustrated in FIG. 7A, the first protruding portions 20a may be separately formed to respectively correspond to the protruding portions ILD1a of the lower insulating layer ILD1. In this case, the first protruding portions 20a may overlap in a one-to-one manner the protruding portions ILD1a of the lower insulating layer ILD1 in a plan view.

The insulating gapfill layer 20 may include a material having an etch selectivity with respect to the lower and upper sacrificial patterns LP and UP. For example, the insulating gapfill layer 20 may be formed of or include silicon oxide. The insulating gapfill layer 20 may be formed at a deposition rate higher than that of the lower insulating layer ILD1. For example, the insulating gapfill layer 20 may be formed by a deposition technique which can realize a higher deposition rate than that of the deposition technique (e.g., HDP CVD) for the lower insulating layer ILD1. For example, the insulating gapfill layer 20 may include a TEOS layer formed by a PE CVD process. In this case, the insulating gapfill layer 20 may have a density lower than that of the lower insulating layer ILD1.

Referring to FIGS. 3, 6F, 7B, and 8B, the second protruding portions 20b of the insulating gapfill layer 20 may be partially removed. The partial removal of the second protruding portions 20b of the insulating gapfill layer 20 may include forming a mask pattern on the insulating gapfill layer 20 to expose the cell array regions CAR and then etching the second protruding portions 20b of the insulating gapfill layer 20 using the mask pattern as an etch mask (e.g., in an anisotropic manner). Accordingly, it may be possible to reduce the thickness of the insulating gapfill layer 20 on the cell array regions CAR. Portions 20c of the second protruding portions 20b of the insulating gapfill layer 20 may remain after the removal process. In certain embodiments, the removal process may be omitted.

Referring to FIGS. 3, 6G, and 7C, a first planarization process may be performed to remove the first protruding portions 20a and the remaining second protruding portions 20c of the insulating gapfill layer 20. The first planarization process may be performed in such a way that the etch stop patterns ES are not exposed. Accordingly, after the first planarization process, the insulating gapfill layer 20 may have a top surface at a level higher than that of top surfaces of the etch stop patterns ES. The first planarization process may be performed using, for example, a chemical mechanical polishing (CMP) process. In certain embodiments, the first planarization process may be omitted.

Referring to FIGS. 3 and 6H, a second planarization process may be performed to expose the etch stop patterns ES. The second planarization process may be performed using a low dishing CMP process. The insulating gapfill layer 20, on which the second planarization process has been performed, may be used as the upper insulating layer ILD2.

The low dishing CMP process may be performed using a polishing slurry, which includes polishing particles (e.g., $CeO_2$ nano particles), an anti-dishing agent, and deionized water. The anti-dishing agent may be formed of or include an organic material (e.g., an organic polymer). The anti-dishing agent may have having a smaller size than the polishing particles. During the low dishing CMP process, the etch stop patterns ES may be charged to have a first polarity (e.g., a positive polarity), and the insulating gapfill layer 20 (e.g., the upper insulating layer ILD2) may be charged to have a second polarity (e.g., a negative polarity) different from the first polarity.

In addition, during the low dishing CMP process, the polishing particles and the anti-dishing agent may also be charged to have the first polarity (e.g., the positive polarity). Since the polarity of the charged polishing particles is the same as that of the charged etch stop patterns ES, but is different from that of the charged insulating gapfill layer 20, if the etch stop patterns ES are exposed, the polishing particles may be concentrated on the insulating gapfill layer 20. Thus, the insulating gapfill layer 20 may be excessively removed.

However, in the case of the low dishing CMP process according to some embodiments, when the etch stop patterns ES are exposed, the anti-dishing agent may be concentrated on the insulating gapfill layer 20 in advance of the polishing particles, because the anti-dishing agent has the same polarity as the polishing particles but a smaller size than the polishing particles. The anti-dishing agent concentrated on the insulating gapfill layer 20 may protect the insulating gapfill layer 20. Furthermore, since the anti-dishing agent is repulsively interacted with the polishing particles, the anti-dishing agent may prevent or suppress the polishing particles from being concentrated on the insulating gapfill layer 20. As a result, it may be possible to prevent the insulating gapfill layer 20 from being excessively removed.

After the second planarization process, the upper insulating layer ILD2 may have a concavely-recessed top surface. However, since the second planarization process is performed using the low dishing CMP process, the top surface of the upper insulating layer ILD2 may have a small recess depth. As an example, the recess depth of the top surface of the upper insulating layer ILD2 may be less than a thickness of the etch stop pattern ES. As another example, the lowermost level of the top surface of the upper insulating layer ILD2 may be higher than a level of bottom surfaces of the etch stop pattern ES.

Referring to FIGS. 3 and 6I, the etch stop patterns ES may be removed. The etch stop patterns ES may be removed by a wet-etching process, in which an etch recipe having an etch selectivity with respect to the upper insulating layer ILD2 is used. For example, the etch stop patterns ES may be removed by a wet etching process, in which an etching solution containing phosphoric acid is used. As a result of the removal of the etch stop patterns ES, the upper insulating layer ILD2 may have a protruded portion ILD2a whose top surface is higher than that of the mold structure MS.

Referring to FIGS. 3 and 6J, the protruded portion ILD2a of the upper insulating layer ILD2 may be at least partially removed. For this, a third planarization process may be performed on the protruded portion ILD2a of the upper insulating layer ILD2. In some embodiments, the third planarization process may be performed to allow the upper insulating layer ILD2 to have a substantially flat top surface.

Figure 8A:
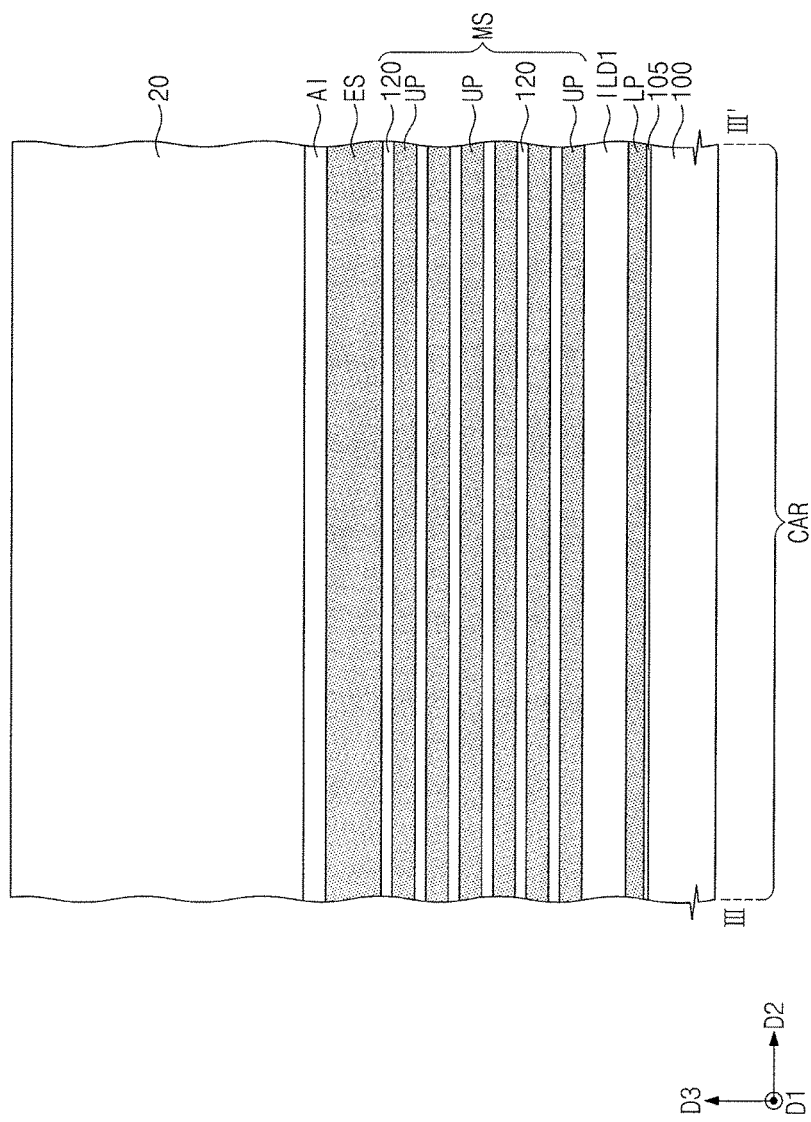
FIGS. 8A-8G illustrate are sectional views taken along another section line in FIG. 3.
Figure 8B:
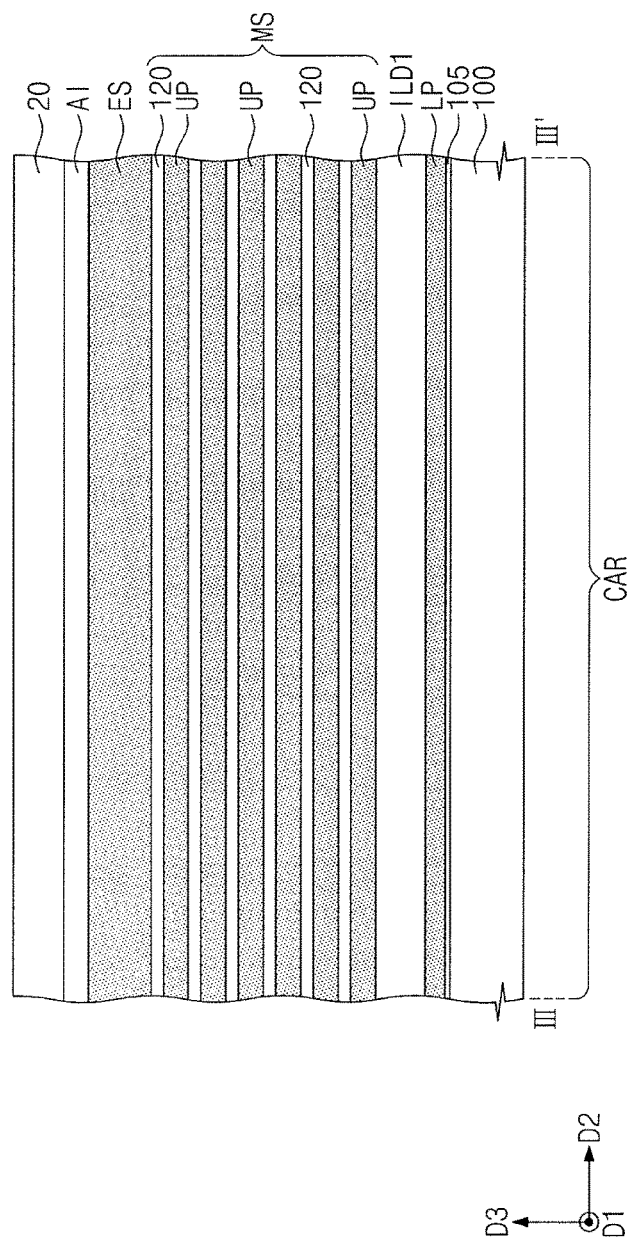
Figure 8C:
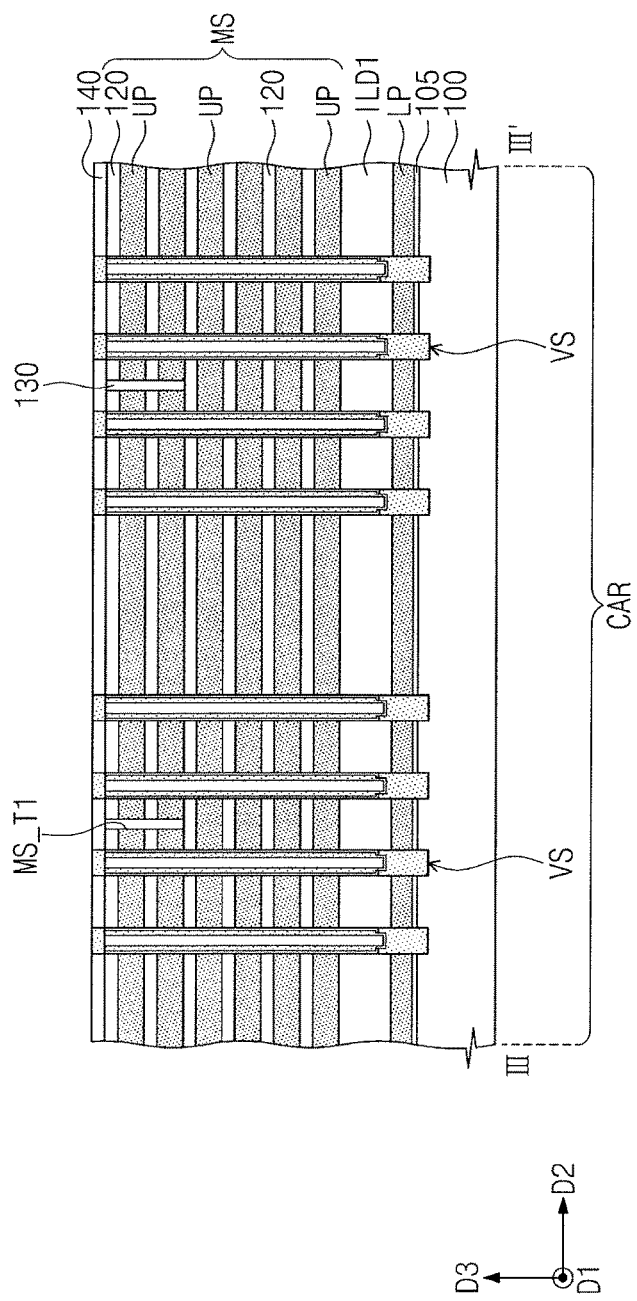

Referring to FIGS. 3, 6K, and 8C, the insulating separation layer 130 extending in the first direction D1 may be formed in an upper portion of each of the mold structures MS. The formation of the insulating separation layer 130 may include forming a first separation trench MS_T1 to separate the uppermost and next-uppermost ones of the upper sacrificial patterns UP in the second direction D2 and then forming the insulating separation layer 130 to fill the first separation trench MS_T1.

The first interlayered insulating layer 140 may be formed to cover the mold structures MS, the insulating separation layer 130, and the upper insulating layer ILD2. In some embodiments, formation of the first interlayered insulating layer 140 may be omitted.

The vertical structures VS may be formed on the cell array regions CAR. Each vertical structure VS may be formed to sequentially penetrate the first interlayered insulating layer 140, the mold structure MS, the lower insulating layer ILD1, lower sacrificial pattern LP, and the buffer insulating layer 105. Each vertical structure VS may include the lower semiconductor pattern LSP, the upper semiconductor pattern USP, the insulating filler pattern VI, the vertical insulating pattern VP, and the conductive pad CP. The vertical structures VS may be formed, for example, to have substantially the same features as those described with reference to FIGS. 3, 4A to 4C, and 5.

The dummy vertical structures DVS may be formed on the connection regions CNR to have substantially the same structural features as the vertical structures VS. The dummy vertical structures DVS may penetrate end portions of the upper and lower sacrificial patterns UP and LP.

Figure 8D:
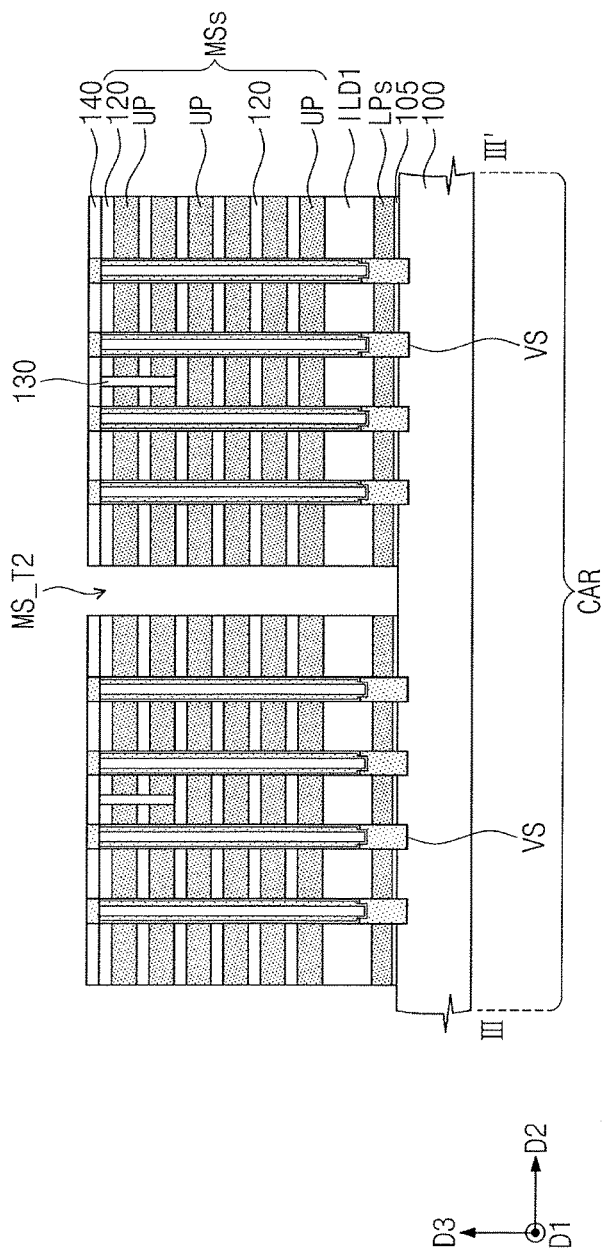

Referring to FIGS. 3 and 8D, the first interlayered insulating layer 140, the mold structures MS, the upper insulating layer ILD2, the lower insulating layer ILD1, the lower sacrificial patterns LP, and the buffer insulating layer 105 may be patterned to form line-shaped second separation trenches MS_T2 extending in the first direction D1. Each of the second separation trenches MS_T2 may be formed to expose the top surface of the substrate 100. The second separation trenches MS_T2 may divide each of the mold structures MS into mold structure segments MSs, which are spaced apart from each other in the second direction D2, and divide each of the lower sacrificial patterns LP into lower sacrificial pattern segments LPs which are spaced apart from each other in the second direction D2.

Figure 8E:
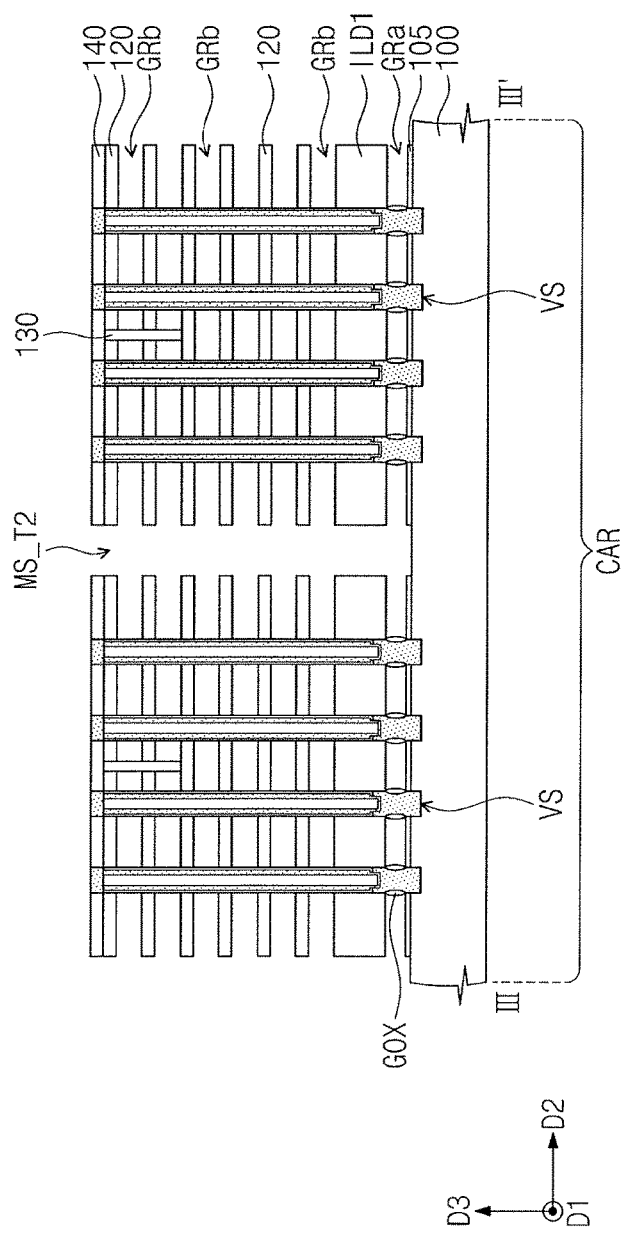

Referring to FIGS. 3, 6L, and 8E, the lower and upper sacrificial patterns LP and UP exposed by the second separation trenches MS_T2 may be removed. Regions from which the lower sacrificial patterns LP are removed may be referred to as lower gap regions GRa. Regions from which the upper sacrificial patterns UP are removed may be referred to as upper gap regions GRb. Removal of the lower and upper sacrificial patterns LP and UP may be performed using an etching recipe having an etch selectivity with respect to the substrate 100, the buffer insulating layer 105, the lower insulating layer ILD1, the upper insulating layer ILD2, the insulating patterns 120, and the vertical structures VS. In the case where the buffer insulating layer 105, the lower insulating layer ILD1, the upper insulating layer ILD2, and the insulating patterns 120 include silicon oxide and the lower and upper sacrificial patterns LP and UP include silicon nitride, the etching process may be performed using an etching solution containing phosphoric acid.

The upper gap regions GRb may horizontally extend from the second separation trenches MS_T2 and may be formed between the insulating patterns 120. The upper gap regions GRb may be formed to partially expose side surfaces of the vertical structures VS.

The lower gap regions GRa may extend from the second separation trenches MS_T2 and may be formed between the buffer insulating layer 105 and the lower insulating layer ILD1. Each of the lower gap regions GRa may be formed to partially expose the side surface of the lower semiconductor pattern LSP.

The gate insulating layer GOX may be formed on the side surface of the lower semiconductor pattern LSP exposed by the lower gap region GRa. For example, the gate insulating layer GOX may be formed by thermally oxidizing portions of the lower semiconductor pattern LSP exposed by the lower gap regions GRa.

Figure 8F:
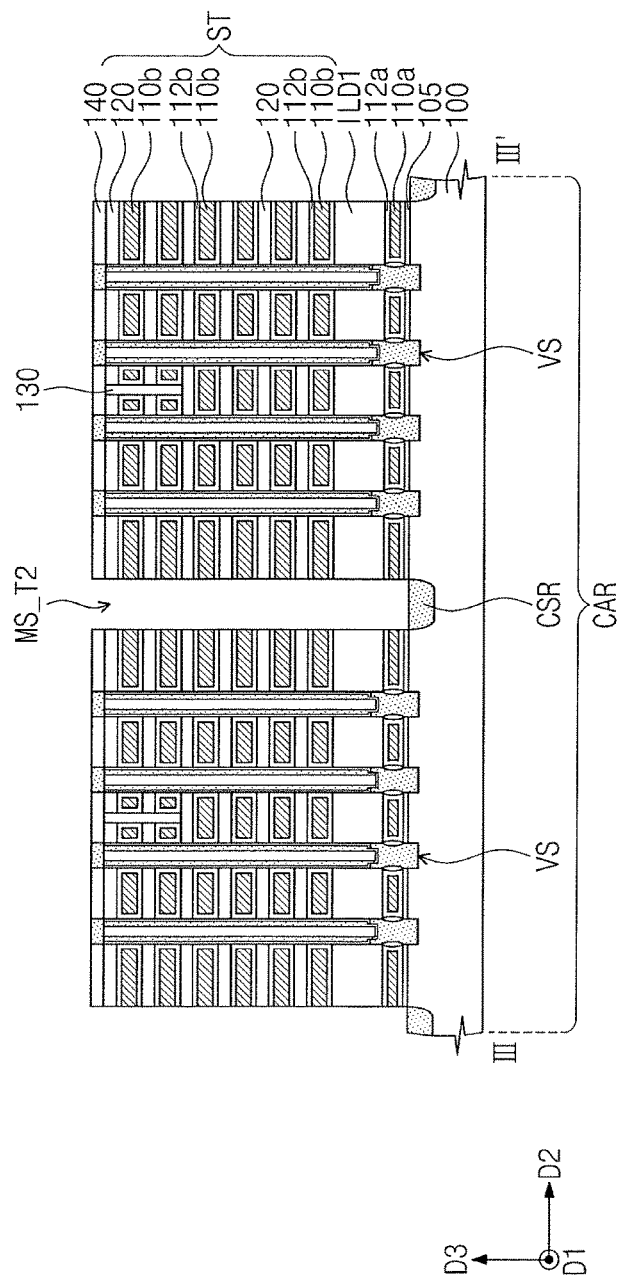

Referring to FIGS. 3, 6M, and 8F, the lower horizontal insulating pattern 112a may be formed to conformally cover an inner surface of each of the lower gap regions GRa. The upper horizontal insulating pattern 112b may be formed to conformally cover an inner surface of each of the upper gap regions GRb. The lower conductive pattern 110a may be formed in each of the lower gap regions GRa. The upper conductive pattern 110b may be formed in each of the upper gap regions GRb. Accordingly, in each stack ST, the upper conductive patterns 110b and the insulating patterns 120 may be alternately and repeatedly stacked, and the stacks ST may be formed on the lower insulating layer ILD1.

Formation of the lower and upper horizontal insulating patterns 112a and 112b and the lower and upper conductive patterns 110a and 110 may include forming an insulating layer to conformally cover inner surfaces of the gap regions GRa and GRb, forming a conductive layer to fill the gap regions GRa and GRb, and removing portions of the insulating and conductive layers from a region outside the gap regions GRa and GRb.

The common source regions CSR may be formed in the substrate 100 exposed by the second separation trenches MS_T2. Formation of the common source regions CSR may include doping the substrate 100 exposed by the second separation trenches MS_T2 with impurities. The common source regions CSR may be doped to have a second conductivity type (e.g., n-type) that is different from the first conductivity type.

Figure 8G:
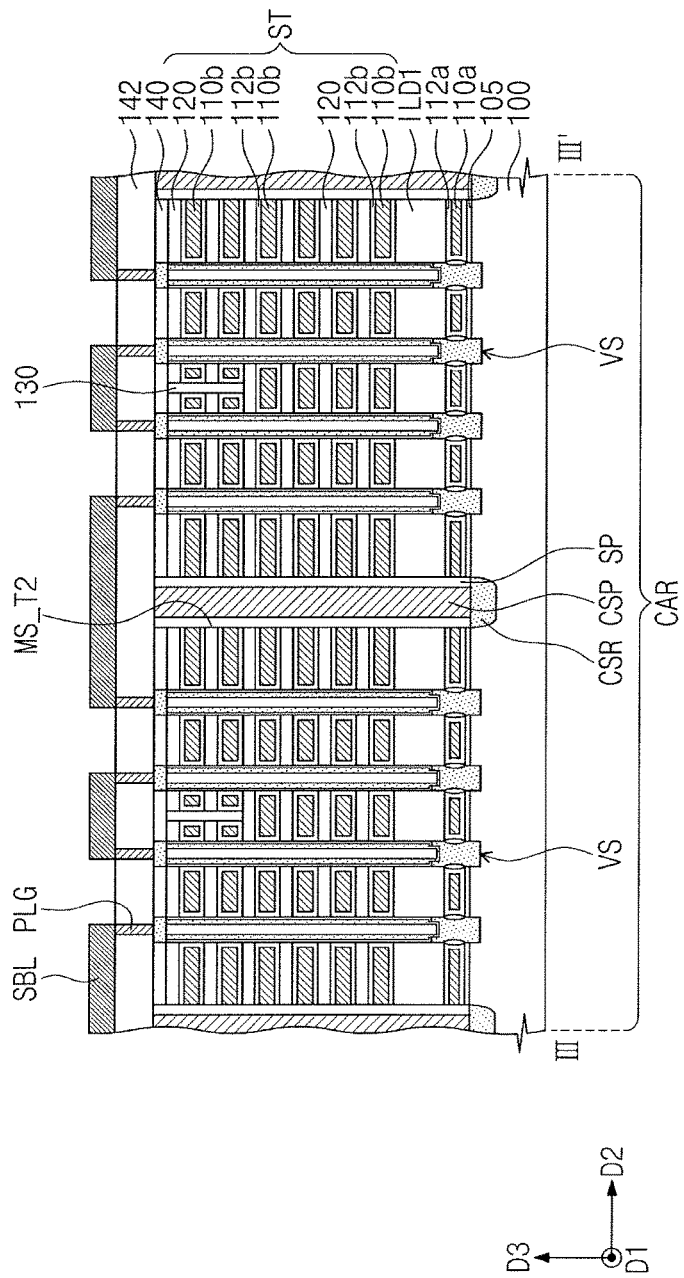

Referring to FIGS. 3, 6N, and 8G, the common source plugs CSP may be formed in the second separation trenches MS_T2 and may be coupled to the common source regions CSR. In addition, the insulating spacers SP may be formed between the common source plugs CSP and the stacks ST.

The second interlayered insulating layer 142 may be formed to cover the first interlayered insulating layer 140. The second interlayered insulating layer 142 may also cover the vertical structures VS and the common source plugs CSP.

The contact plugs PLG, the cell contact plugs CPLG, and the peripheral contact plugs PPLG may be formed on the substrate 100. The contact plugs PLG, the cell contact plugs CPLG, and the peripheral contact plugs PPLG may be formed to have substantially the same features as those described with reference to FIGS. 3 and 4A to 4C.

The sub-bit lines SBL, the connection lines CL, and the peripheral circuit lines PCL may be formed on the second interlayered insulating layer 142. The sub-bit lines SBL, the connection lines CL, and the peripheral circuit lines PCL may be formed, for example, to have substantially the same features as those described in FIGS. 3 and 4A to 4C.

Referring back to FIGS. 3, 4A to 4C, and 5, the third interlayered insulating layer 144 may be formed on the second interlayered insulating layer 142. The third interlayered insulating layer 144 may cover the sub-bit lines SBL, the connection lines CL, and the peripheral circuit lines PCL.

The bit lines BL may be formed on the third interlayered insulating layer 144. The bit lines BL may cross the stacks ST or extend in the second direction D2 and may be coupled to the sub-bit lines SBL through the bit line contact plugs BPLG.

In a method of fabricating a semiconductor device according to some embodiments, the stacks ST and the vertical structures VS may be formed on the lower insulating layer ILD1, on which a planarization process is not performed. Accordingly, it may be possible to prevent defects (e.g., scratch) from being formed on the top surface of the lower insulating layer ILD1 by a planarization process. Thus, it may be possible to improve reliability of the semiconductor device.

In a method of fabricating a semiconductor device according to some embodiments, a planarization process on the lower insulating layer ILD1 may be omitted. Thus, it may be possible to simplify the process of fabricating the semiconductor device. This may make it possible to reduce the fabrication cost of the semiconductor device.

FIGS. 9A to 9D are sectional views illustrating various stages of another embodiment of a method for fabricating a three-dimensional semiconductor device. For example, FIGS. 9A to 9D are sectional views corresponding to line I-I' of FIG. 3, and may correspond to process steps to be performed after the process steps described with reference to FIGS. 6A to 6E.

Figure 9A:
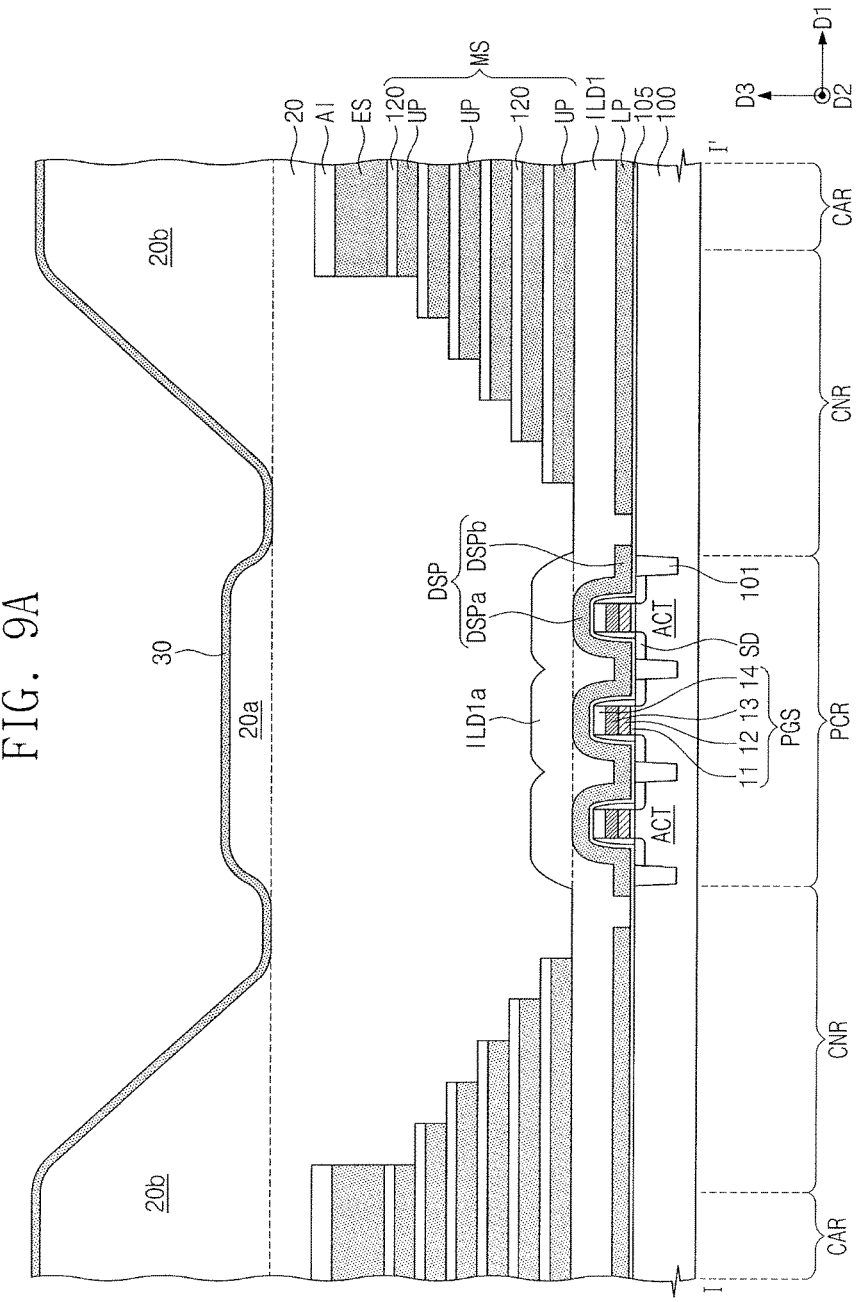
FIGS. 9A-9D illustrate various stages of another embodiment of a method for fabricating a three-dimensional semiconductor device.

Referring to FIGS. 3 and 9A, an etch stop layer 30 may be formed to cover the insulating gapfill layer 20. The etch stop layer 30 may include a material having an etch selectivity with respect to the insulating gapfill layer 20. For example, the etch stop layer 30 may be formed of or include silicon nitride or silicon oxynitride.

Figure 9B:
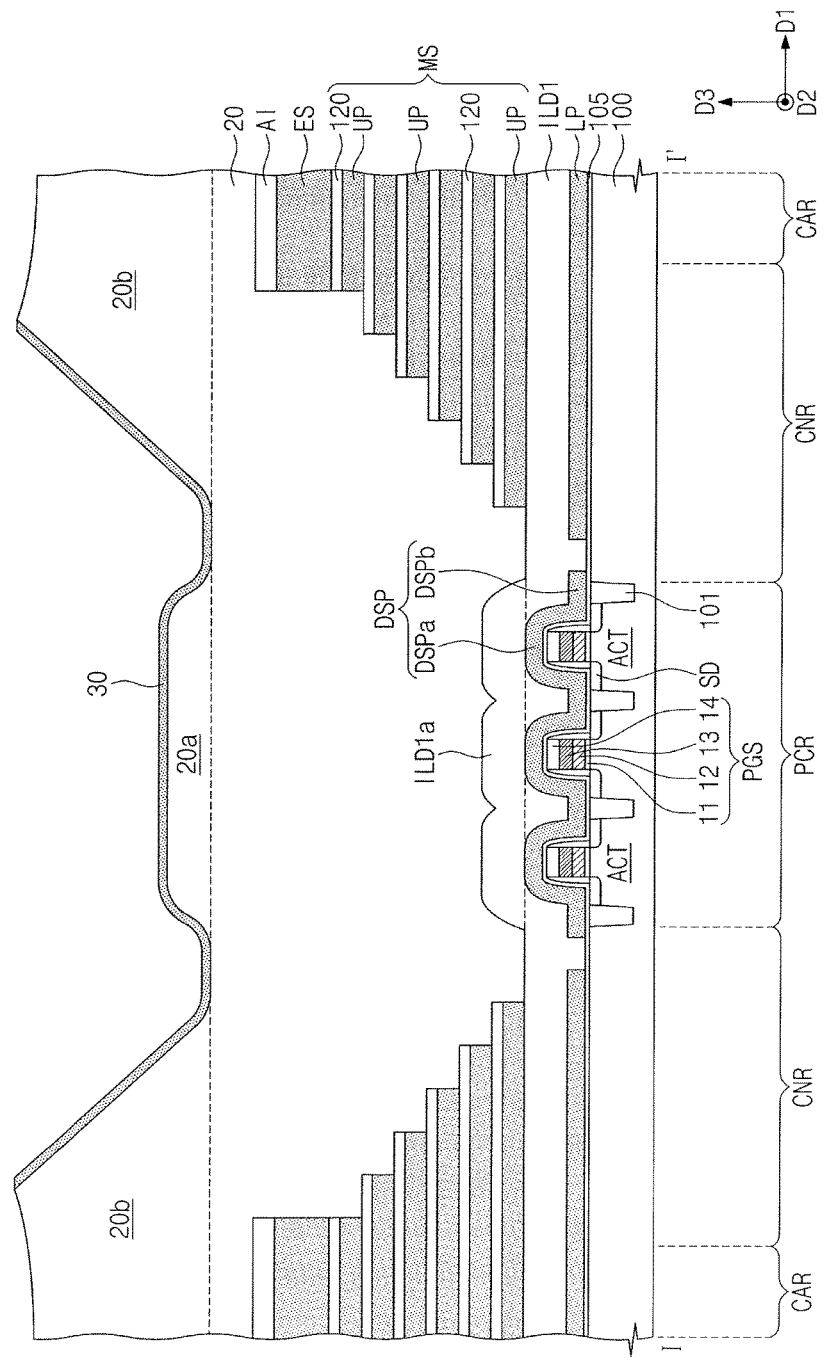

Referring to FIGS. 3 and 9B, a first planarization process may be performed to partially remove upper portions of the second protruding portions 20b of the insulating gapfill layer 20. The first planarization process may be performed using a CMP process, in which an etch rate of the etch stop layer 30 is higher than that of the insulating gapfill layer 20. The first planarization process may be performed to expose the insulating gapfill layer 20 on the cell array regions CAR.

Figure 9C:
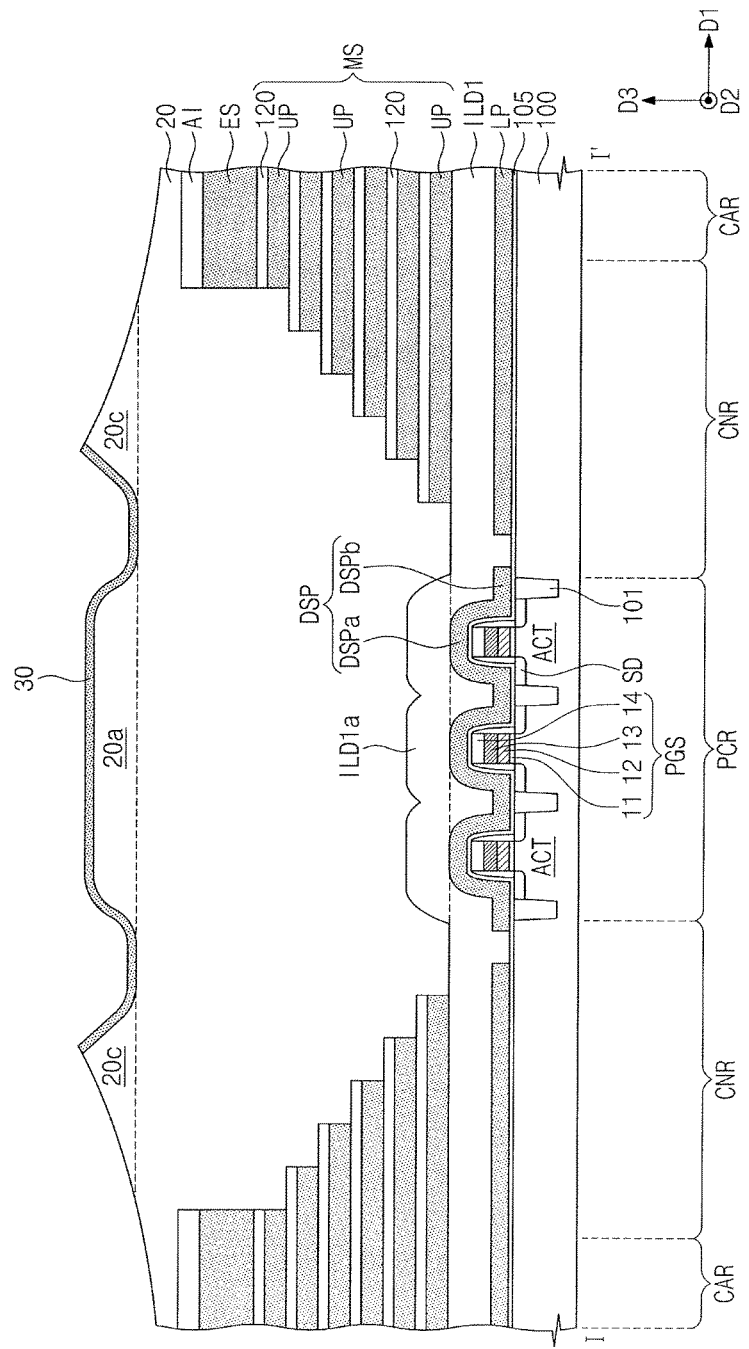

Referring to FIGS. 3 and 9C, a second planarization process may be performed to partially remove the second protruding portions 20b of the insulating gapfill layer 20. The second planarization process may be performed using a CMP process, in which an etch rate of the insulating gapfill layer 20 is higher than that of the etch stop layer 30. The second planarization process may be performed to remain portions 20c of the second protruding portions 20b of the insulating gapfill layer 20 on, for example, the connection regions CNR.

Figure 9D:
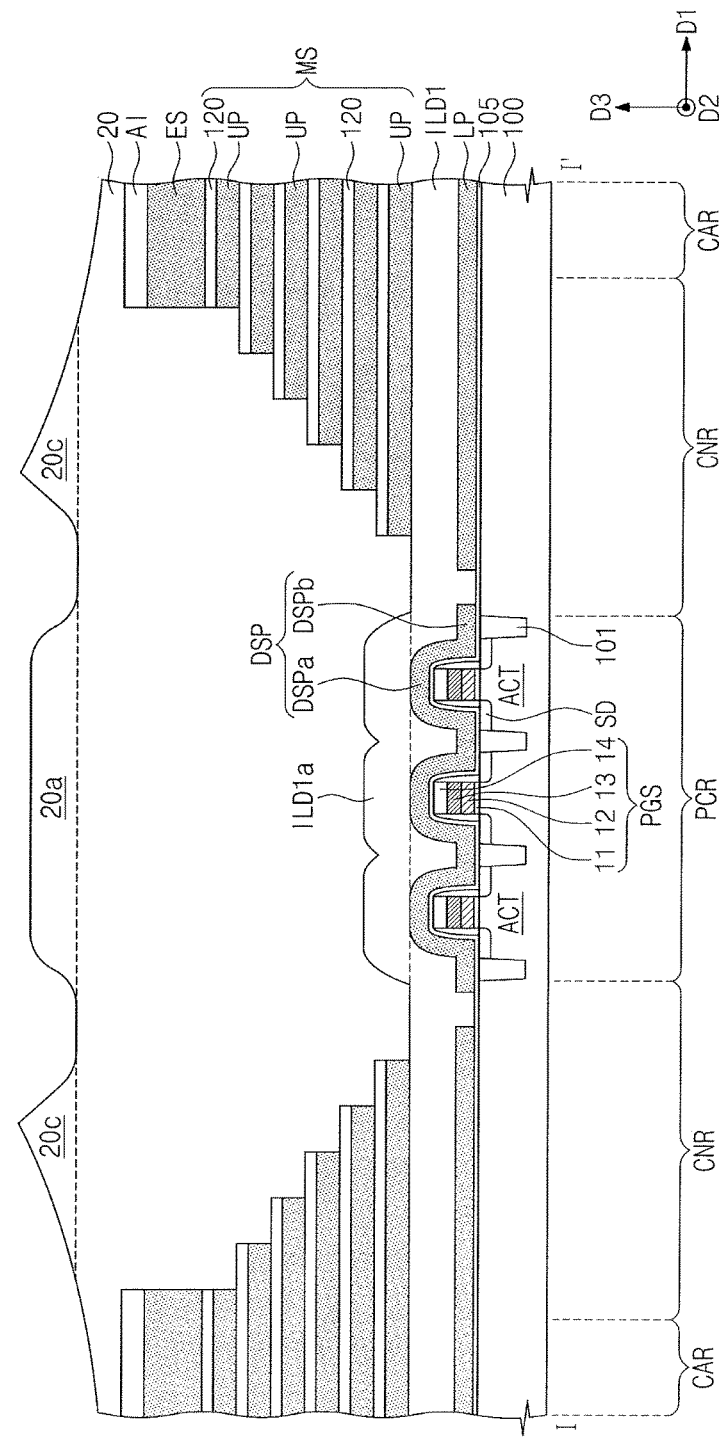

Referring to FIGS. 3 and 9D, the etch stop layer 30 may be removed. The etch stop layer 30 may be removed by a wet-etching process, in which an etch recipe having an etch selectivity with respect to the insulating gapfill layer 20 is used. For example, the etch stop layer 30 may be removed by a wet etching process, in which an etching solution containing phosphoric acid is used. As a result of the removal of the etch stop layer 30, the first protruding portions 20a of the insulating gapfill layer 20 may be exposed.

Thereafter, the process steps described with reference to FIGS. 6H to 6N and FIG. 4A may be performed in substantially the same manner. In such embodiments, the first protruding portions 20a may be removed by the low dishing CMP process.

FIGS. 10A to 10E are sectional views illustrating various stages of another embodiment of a method for fabricating a three-dimensional semiconductor device. For example, FIGS. 10A to 10E are sectional views corresponding to line I-I' of FIG. 3, and may correspond to process steps to be performed after the process steps described with reference to FIGS. 6A to 6D.

Figure 10A:
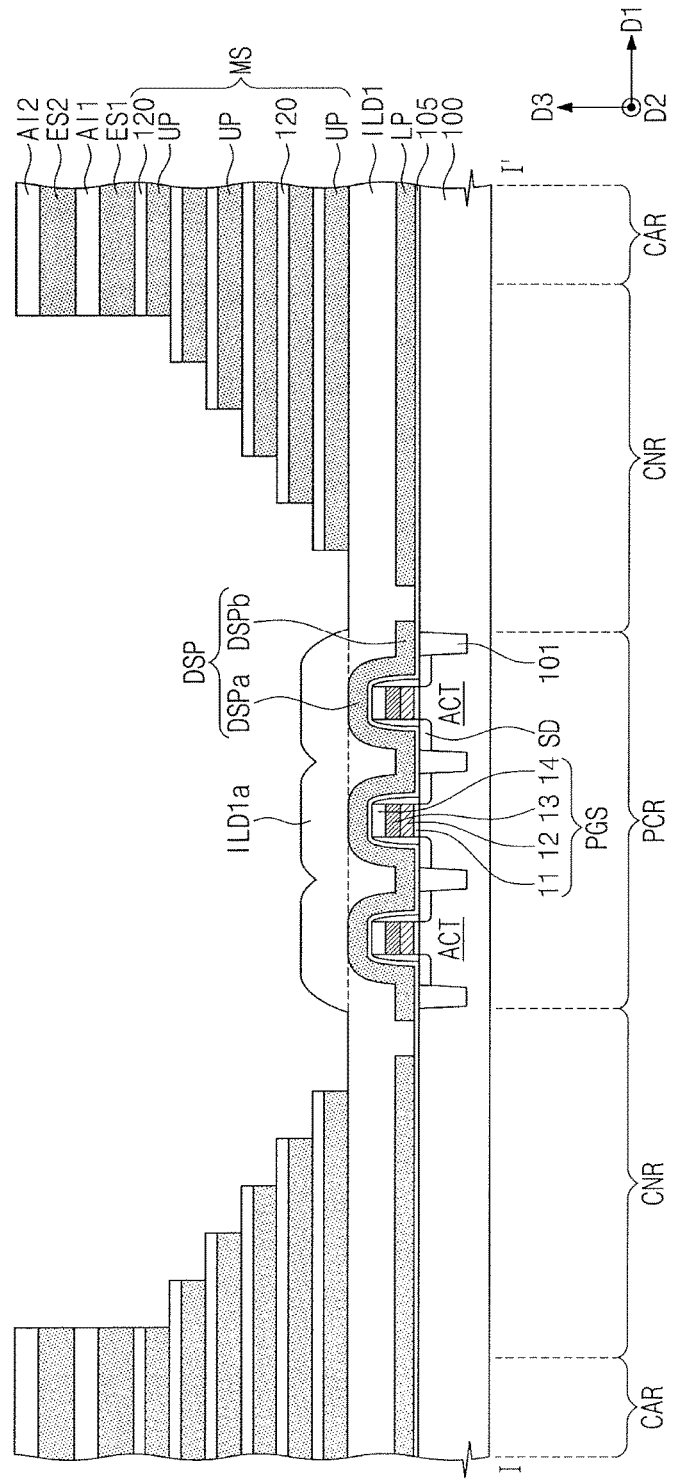
FIGS. 10A-10E illustrate various stages of another embodiment of a method for fabricating a three-dimensional semiconductor device.

Referring to FIGS. 3 and 10A, the etch stop patterns ES of FIG. 6D may be referred to as first etch stop patterns ES1 and the additional insulating patterns AI of FIG. 6D may be referred to as first additional insulating patterns AI1.

Second etch stop patterns ES2 and second additional insulating patterns AI2 may be sequentially formed on the first additional insulating patterns AI1. The second etch stop patterns ES2 may include a material having an etch selectivity with respect to the insulating gapfill layer 20 as described below. For example, the etch stop patterns ES may be formed of or include silicon nitride or silicon oxynitride. The second additional insulating patterns AI2 may be formed of or include silicon oxide.

Figure 10B:
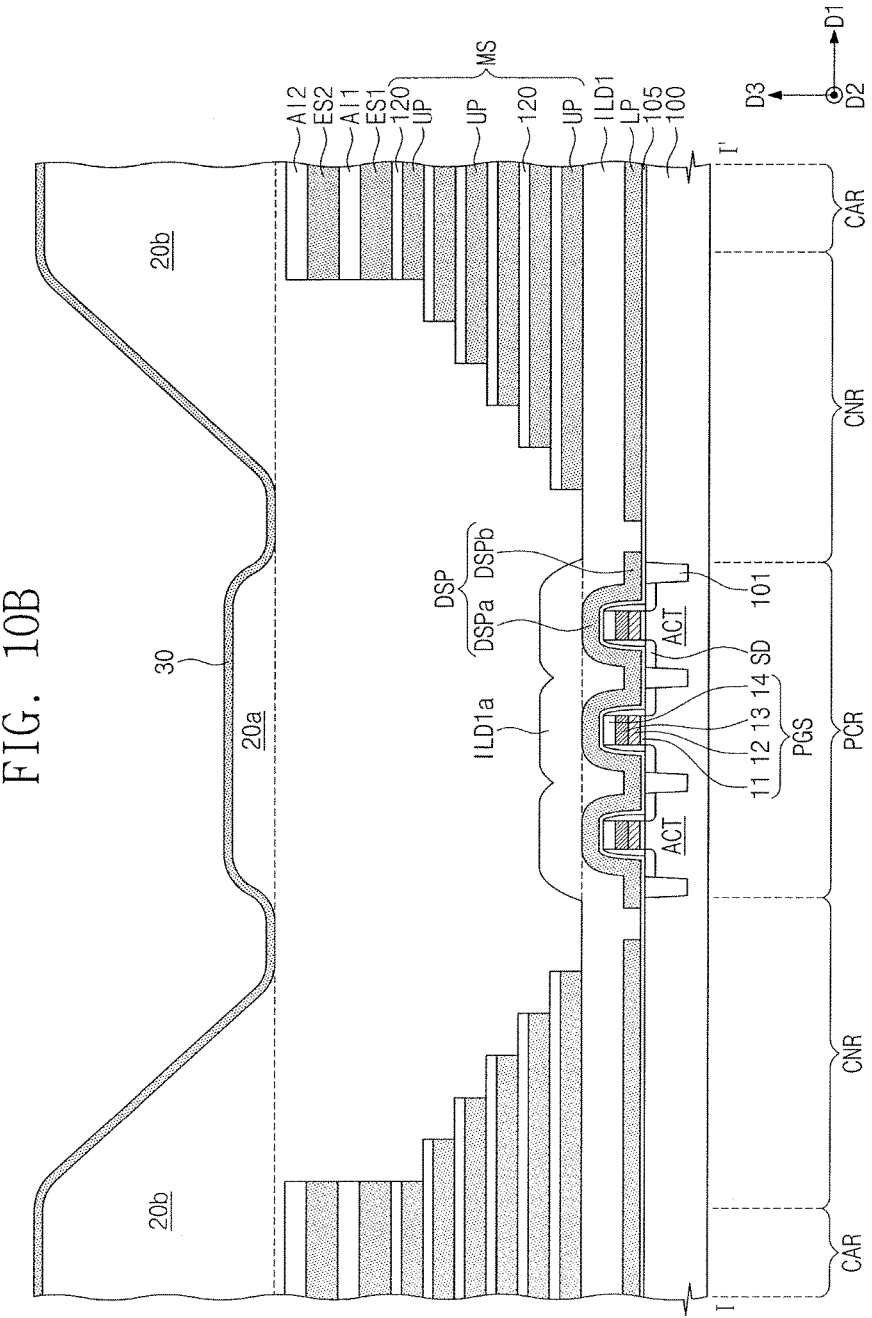

Referring to FIGS. 3 and 10B, the insulating gapfill layer 20 may be formed on the resulting structure with the mold structure MS. The insulating gapfill layer 20 may be formed to have the same features as the insulating gapfill layer 20 as described with reference to FIG. 6E.

The etch stop layer 30 may be formed to cover the insulating gapfill layer 20. The etch stop layer 30 may include a material having an etch selectivity with respect to the insulating gapfill layer 20. For example, the etch stop layer 30 may be formed of or include silicon nitride or silicon oxynitride.

Figure 10C:
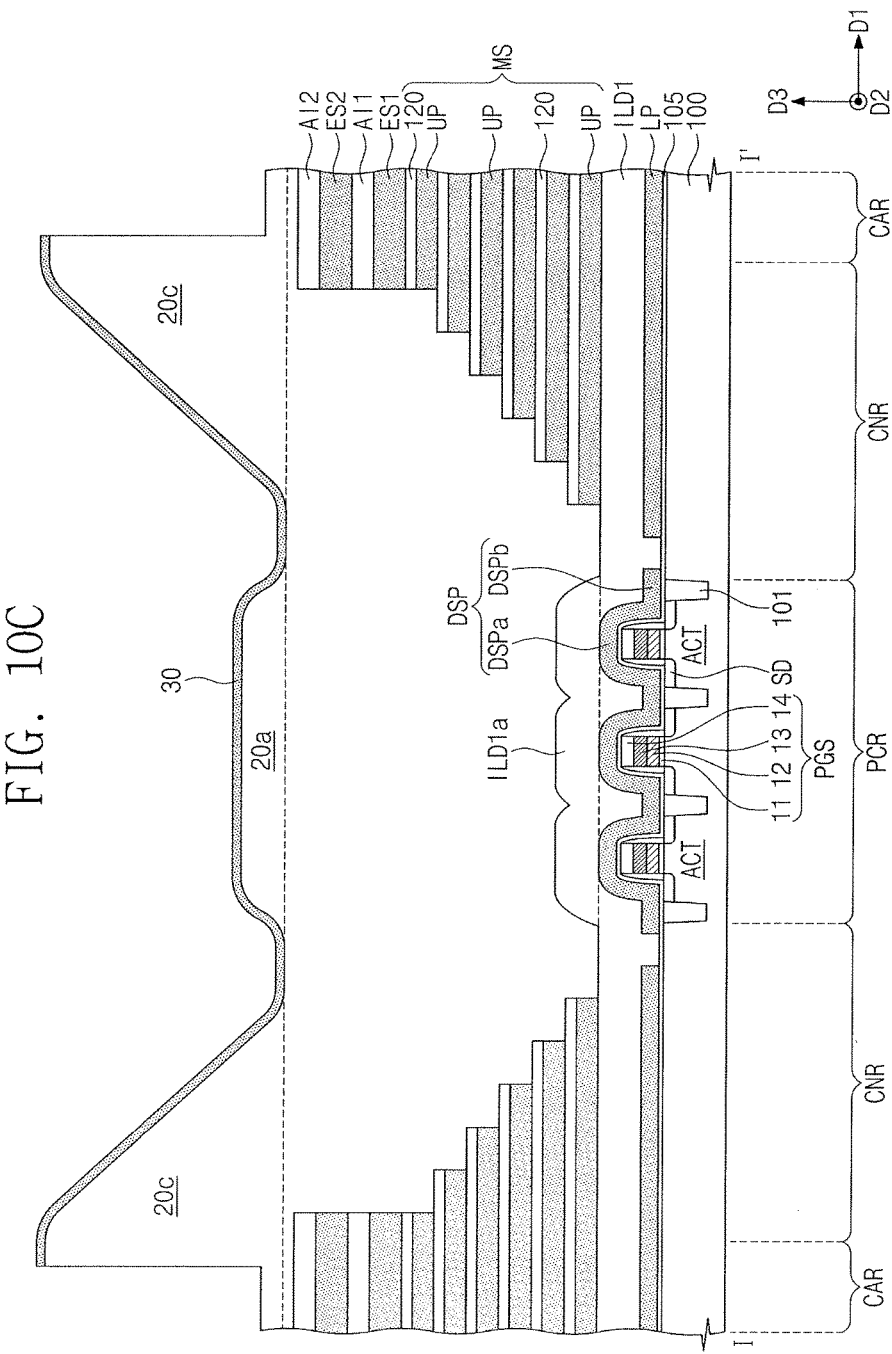

Referring to FIGS. 3 and 10C, the second protruding portions 20b of the insulating gapfill layer 20 may be partially removed. The partial removal of the second protruding portions 20b of the insulating gapfill layer 20 may include forming a mask pattern on the etch stop layer 30 to expose the cell array regions CAR and, then, sequentially and anisotropically etching the etch stop layer 30 and the first protruding portions 20a of the insulating gapfill layer 20 using the mask pattern as an etch mask. Accordingly, it may be possible to reduce the thickness of the insulating gapfill layer 20 on the cell array regions CAR. Portions 20c of the second protruding portions 20b of the insulating gapfill layer 20 may remain after the removal process.

Figure 10D:
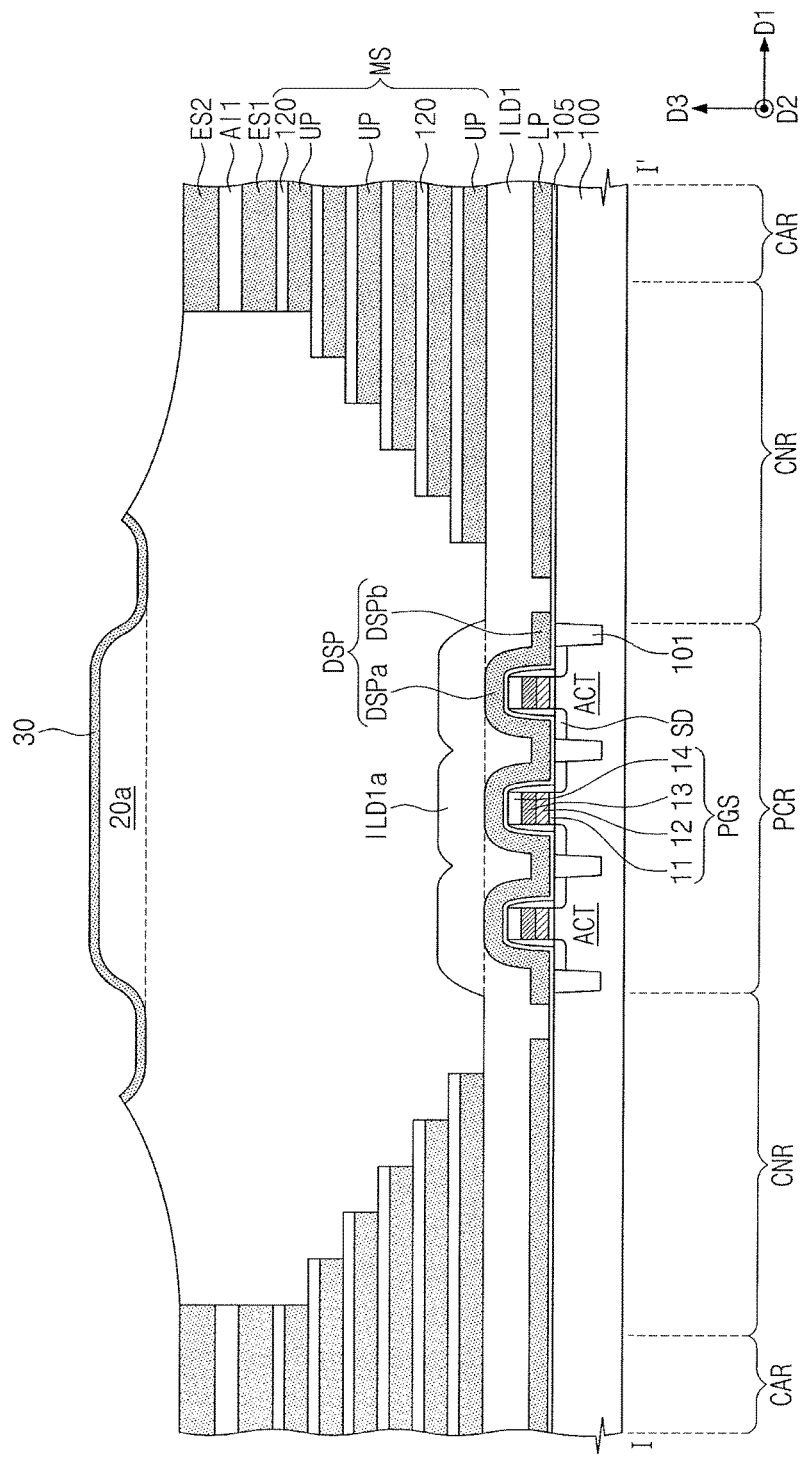

Referring to FIGS. 3 and 10D, a first planarization process may be performed to at least partially remove the remaining portions 20c of the insulating gapfill layer 20. The first planarization process may be performed to expose the second etch stop patterns ES2. The first planarization process may be performed by a CMP process, which is selected to allow the insulating gapfill layer 20 to have an etch rate higher than that of the etch stop layer 30. Accordingly, the first protruding portions 20a and a portion of etch stop layer 30 covering the first protruding portions 20a may not be removed by the first planarization process.

Figure 10E:
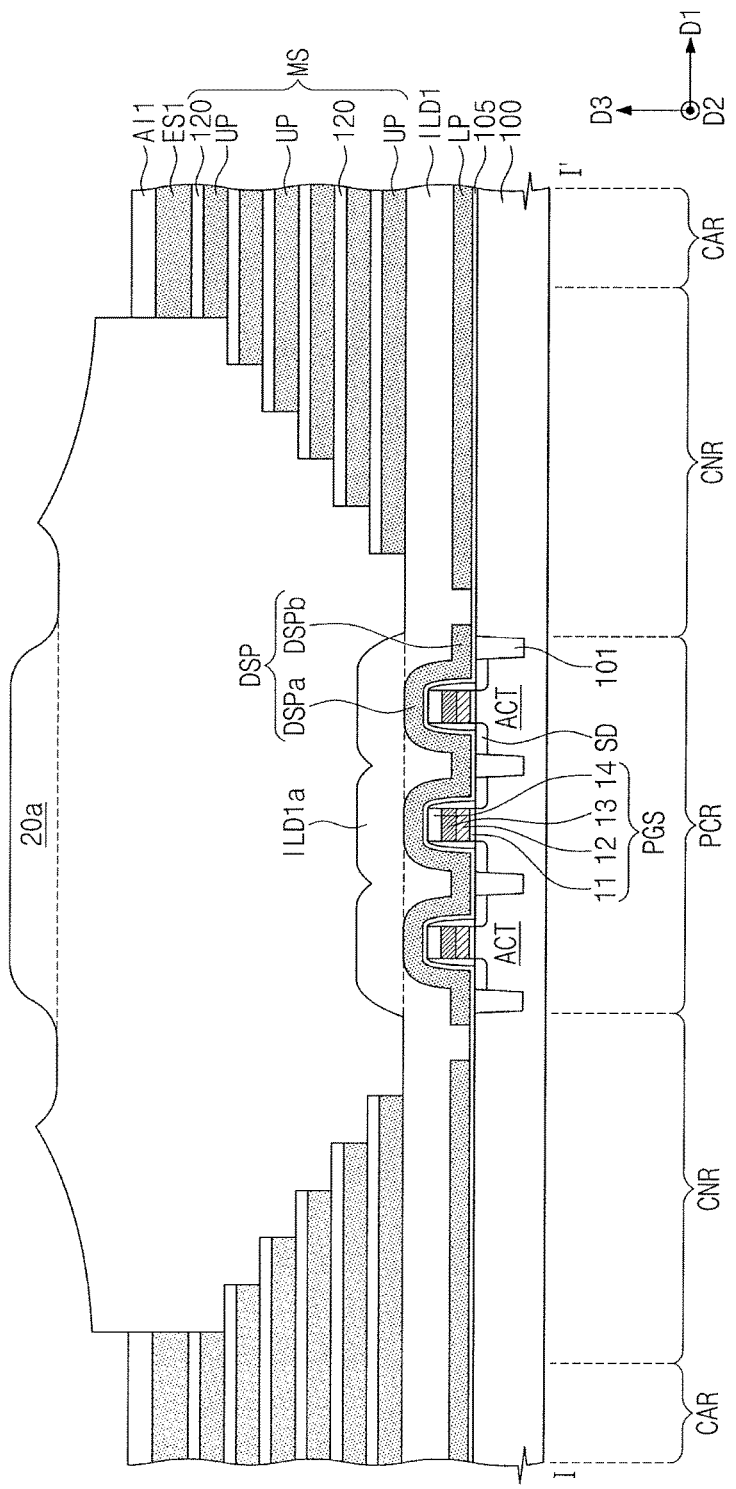

Referring to FIGS. 3 and 10E, the etch stop layer 30 and the second etch stop patterns ES2 may be removed. The etch stop layer 30 and the second etch stop patterns ES2 may be removed by a wet-etching process, in which an etch recipe having an etch selectivity with respect to the first additional insulating patterns AI1 and the insulating gapfill layer 20 is used. For example, the etch stop layer 30 and the second etch stop patterns ES2 may be removed by a wet etching process, in which an etching solution containing phosphoric acid is used. As a result of the removal of the etch stop layer 30, the first protruding portions 20a of the insulating gapfill layer 20 may be exposed.

Thereafter, the process steps described with reference to FIGS. 6H to 6N and FIG. 4A may be performed in substantially the same manner. In such embodiments, the first protruding portions 20a may be removed by the low dishing CMP process.

In a semiconductor device according to some embodiments, stacks and vertical structures may be formed on a lower insulating layer, on which a planarization process is not performed. Accordingly, it may be possible to prevent defects (e.g., scratch) from being formed on a top surface of the lower insulating layer by the planarization process. Thus, it may be possible to improve reliability of the semiconductor device.

In a method for fabricating a semiconductor device according to some embodiments, a planarization process on a lower insulating layer may be omitted. Thus, it may be possible to simplify the process of fabricating the semiconductor device. This may make it possible to reduce the fabrication cost of the semiconductor device.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise indicated. Accordingly, various changes in form and details may be made without departing from the spirit and scope of the embodiments set forth in the claims.

What is claimed is:

1. A semiconductor device, comprising:
a substrate including a peripheral circuit region and a cell array region;
a peripheral structure on the peripheral circuit region;
a lower insulating layer covering the peripheral circuit region and the cell array region, the lower insulating layer on the peripheral circuit region having a flat portion and a protruding portion protruding from the flat portion; and
a stack on the lower insulating layer and on the cell array region, wherein the stack includes upper conductive patterns and insulating patterns which are alternately and repeatedly stacked.

2. The semiconductor device as claimed in claim 1, wherein the protruding portion of the lower insulating layer vertically overlaps the peripheral structure.

3. The semiconductor device as claimed in claim 1, wherein a thickness of the lower insulating layer is greater than a thickness of each of the insulating patterns.

4. The semiconductor device as claimed in claim 3, wherein the thickness of the lower insulating layer is greater than three times the thickness of each of the insulating patterns.

5. The semiconductor device as claimed in claim 1, wherein a thickness of the lower insulating layer is larger than a thickness of each of the upper conductive patterns.

6. The semiconductor device as claimed in claim 1, wherein a thickness of the lower insulating layer is greater than three times a thickness of each of the upper conductive patterns.

7. The semiconductor device as claimed in claim 1, wherein the lower insulating layer on the cell array region and the protruding portion have substantially a same thickness.

8. The semiconductor device as claimed in claim 1, wherein the flat portion and the protruding portion have substantially a same thickness.

9. The semiconductor device as claimed in claim 1, wherein a level of a top surface of the protruding portion is higher than a level of a top surface of the lowermost one of the insulating patterns of the stack.

10. The semiconductor device as claimed in claim 1, further comprising:
a dummy sacrificial pattern on the peripheral circuit region and between the lower insulating layer and the peripheral structure.

11. The semiconductor device as claimed in claim 10, further comprising:
a lower conductive pattern on the cell array region and between the lower insulating layer and the substrate.

12. The semiconductor device as claimed in claim 11, wherein:
the dummy sacrificial pattern includes an extended portion between the flat portion and the substrate, and
the extended portion and the lower conductive pattern are at a same level.

13. The semiconductor device as claimed in claim 1, further comprising:
an upper insulating layer directly on the lower insulating layer and having a flat top surface.

14. The semiconductor device as claimed in claim 1, further comprising:
a contact plug penetrating the protruding portion,
wherein the peripheral structure is a peripheral transistor and wherein the contact plug is coupled to a source/drain region of the peripheral transistor.

15. A semiconductor device, comprising:
a substrate including a peripheral circuit region and a cell array region;
a peripheral structure on the peripheral circuit region;
a lower insulating layer covering the peripheral circuit region and the cell array region and having a protruding portion on the peripheral structure; and
a stack on the lower insulating layer and on the cell array region, wherein the stack includes upper conductive patterns and insulating patterns that are alternately and repeatedly stacked and wherein a level of a top surface of the protruding portion is higher than a level of a top surface of a lowermost one of the insulating patterns of the stack.

16. The semiconductor device as claimed in claim 15, wherein a thickness of the lower insulating layer is greater than three times a thickness of each of the insulating patterns.

17. The semiconductor device as claimed in claim 15, wherein a thickness of the lower insulating layer is greater than three times a thickness of each of the upper conductive patterns.

18. The semiconductor device as claimed in claim 15, further comprising:
   a dummy sacrificial pattern between the protruding portion and the peripheral structure.

19. The semiconductor device as claimed in claim 18, further comprising:
   a lower conductive pattern on the cell array region and between the lower insulating layer and the substrate.

20. The semiconductor device as claimed in claim 15, further comprising:
   an upper insulating layer directly on the lower insulating layer and including a flat top surface.

* * * * *